United States Patent [19]
Myers

[11] Patent Number: 5,188,619
[45] Date of Patent: Feb. 23, 1993

[54] INTERNAL THORACTIC ARTERY CATHETER

[75] Inventor: Gene E. Myers, Sarasota, Fla.

[73] Assignee: Gene E. Myers Enterprises, Inc., Sarasota, Fla.

[21] Appl. No.: 690,848

[22] Filed: Apr. 24, 1991

[51] Int. Cl.[5] .................................................. A61M 25/00
[52] U.S. Cl. ..................................... 604/280; 604/264
[58] Field of Search ............... 604/264, 164, 280-284, 604/170, 95; 128/656-658, 772

[56] References Cited

U.S. PATENT DOCUMENTS

| | | | |
|---|---|---|---|
| 4,033,331 | 7/1977 | Guss et al. | 128/657 |
| 4,117,836 | 10/1978 | Erikson . | |
| 4,169,464 | 10/1979 | Obrez | 604/281 |
| 4,279,252 | 7/1981 | Martin . | |
| 4,531,943 | 7/1985 | Van Tassel et al. . | |
| 4,551,292 | 11/1985 | Fletcher et al. . | |
| 4,563,181 | 1/1986 | Wijayarathna et al. . | |
| 4,568,338 | 2/1986 | Todd . | |
| 4,578,058 | 3/1986 | Grandon . | |
| 4,671,795 | 6/1987 | Mulchin . | |
| 4,694,838 | 9/1987 | Wijayarthna et al. | 128/657 |
| 4,738,667 | 4/1988 | Galloway . | |
| 4,747,840 | 5/1988 | Ladika et al. | 604/264 |
| 4,804,359 | 2/1989 | Grunwald et al. . | |
| 4,838,879 | 6/1989 | Tanabe et al. . | |
| 4,902,276 | 2/1990 | Zakko . | |
| 4,905,667 | 3/1990 | Foerster et al. . | |
| 4,909,258 | 3/1990 | Kuntz et al. . | |
| 4,925,445 | 5/1990 | Sakamoto et al. . | |
| 4,935,017 | 6/1990 | Sylvanowicz | 604/280 |
| 4,950,228 | 8/1990 | Knapp, Jr. et al. . | |
| 4,961,731 | 10/1990 | Bodicky et al. . | |
| 4,973,306 | 11/1990 | Ruiz | 128/658 |
| 4,981,477 | 1/1991 | Schon et al. | 604/281 |

OTHER PUBLICATIONS

USCI Grüntzig Dilaca Coronary Dilatation Equipment, C. R. Bard, Inc. 1980.
Catheterization & Cardiovascular Diagnosis 12:261-265 (1986), p. 263.
Catheterization & Cardiovascular Diagnosis 12:341-46 (1986), p. 342.
Catheterization & Cardiovascular Diagnosis 13:414-18 (1987), p. 416.
British Heart Journal 1989; 61:417-20, pp. 417-420.
Catheterization and Cardiovascular Diagnosis 6:439-449 (1980), pp. 440-441.

Primary Examiner—C. Fred Rosenbaum
Assistant Examiner—Ronald Stright, Jr.
Attorney, Agent, or Firm—Patterson & Keough

[57] ABSTRACT

A catheter is provided comprising a first portion of substantially linear shape, a second portion extending from the first portion at an angle in a curved manner, and a third portion. The third portion extends from the second portion in an out of plane manner relative to the first and second portions. The catheter is thus constructed to provide hooked engagement of an internal thoracic artery.

5 Claims, 43 Drawing Sheets

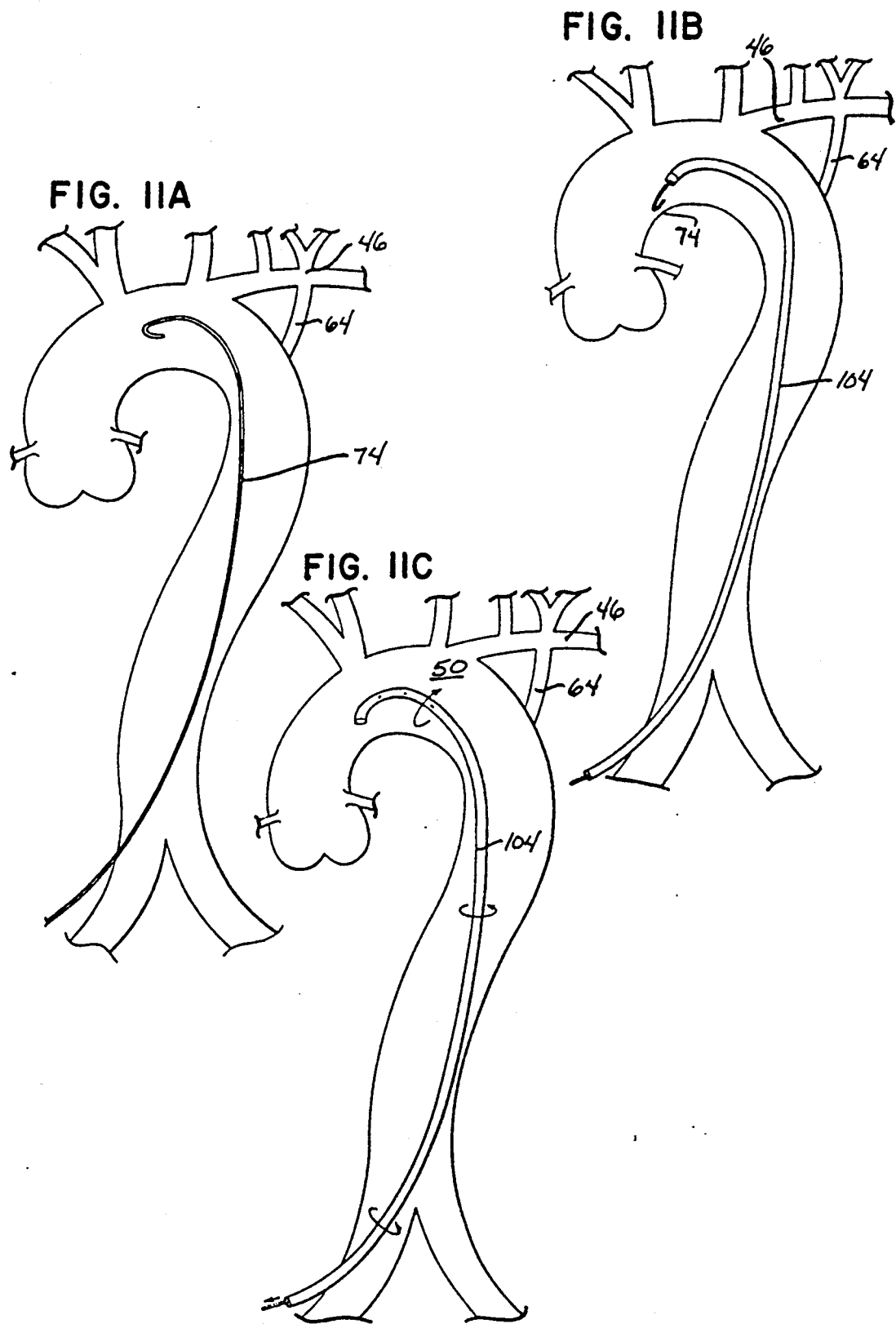

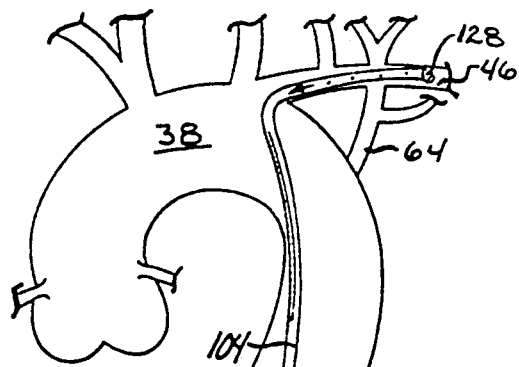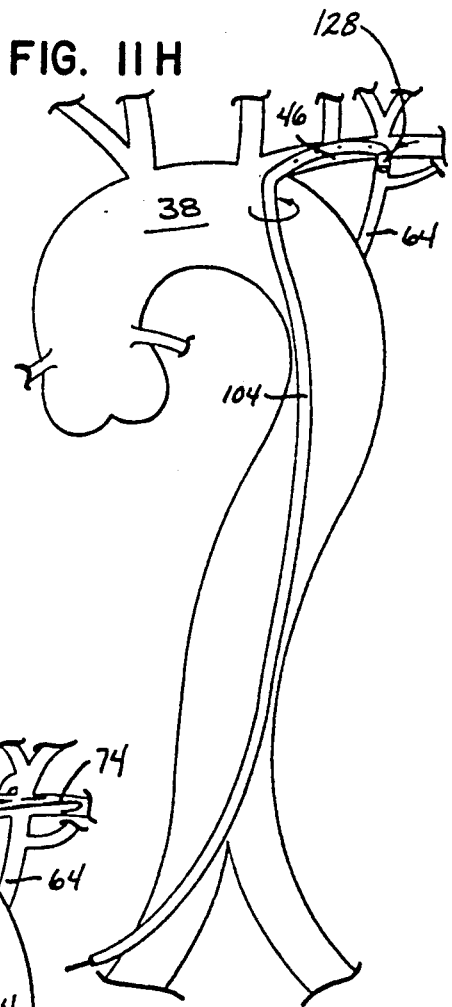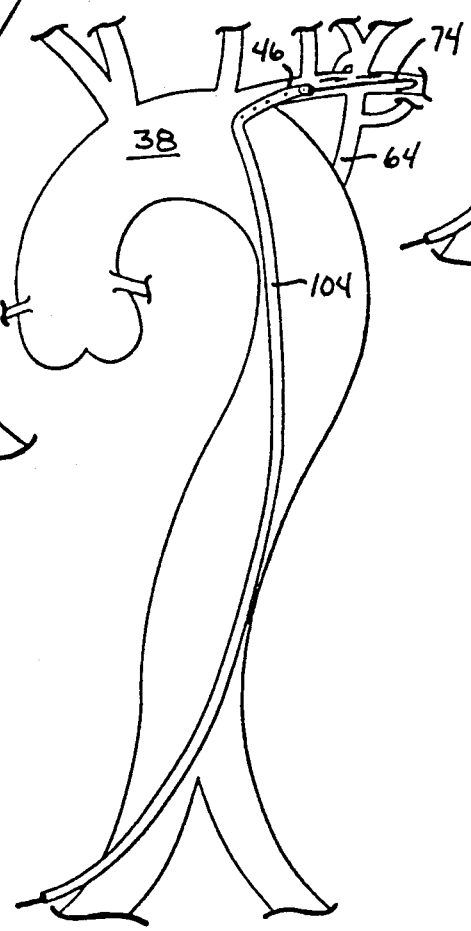

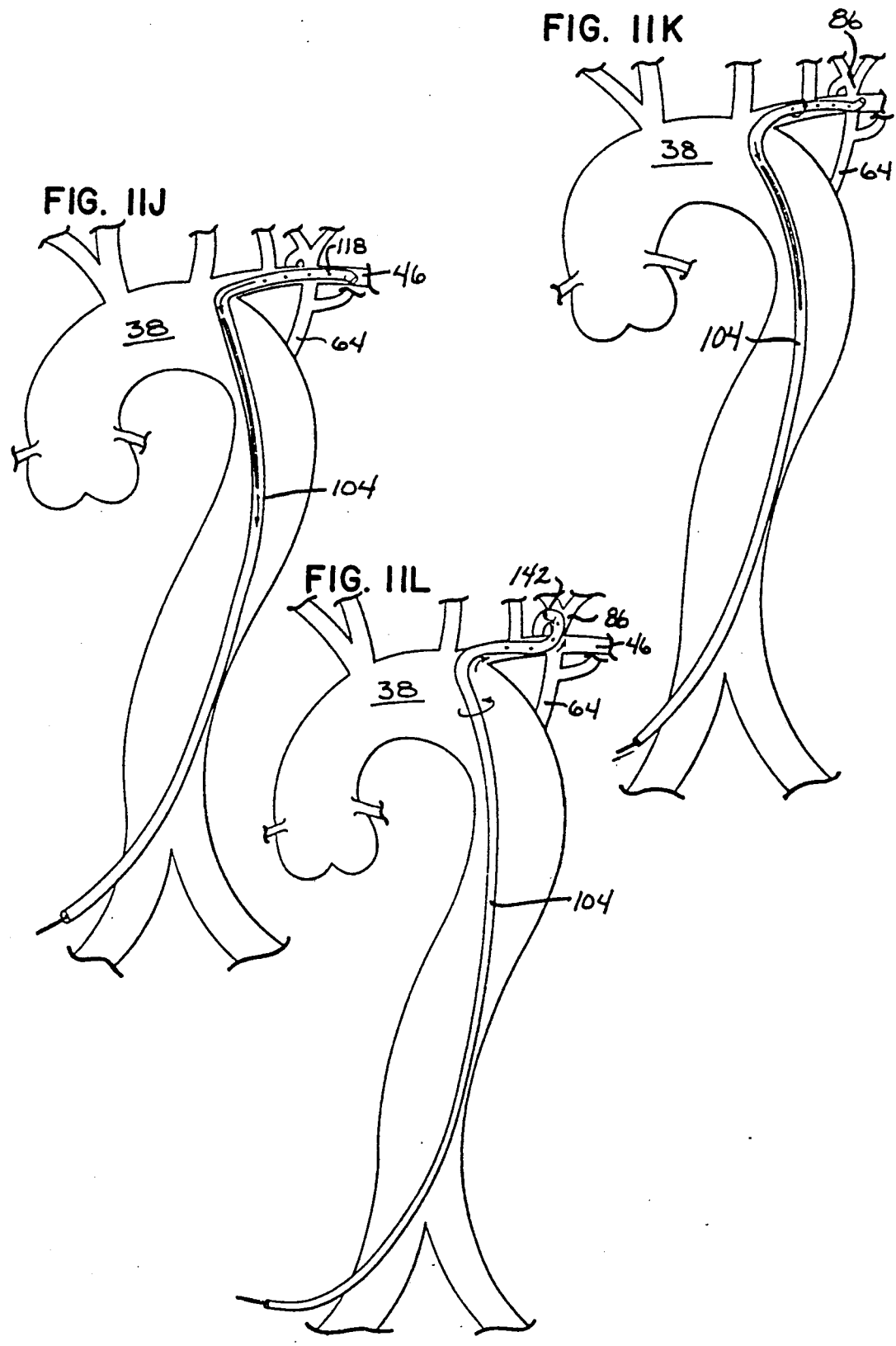

INTERNAL THORACIC ARTERY CATHETER

TECHNICAL FIELD OF THE INVENTION

This invention relates to a method and apparatus to safely, consistently, selectively place a tube or catheter in a normal or geriatrically displaced branch of the aortic arch in order to visualize the arteries pre-operatively and post-operatively and to enlarge the lumen of the arteries or a graft associated therewith.

BACKGROUND OF THE INVENTION

Before the advent of coronary artery bypass surgery (CABG), surgical procedures included dissecting the distal end of a left internal thoracic artery from the sternum and chest wall and using the LITA as a conduit to tunnel into the heart muscle to replenish blood supply secondary to coronary artery blockage in the vessel serving that particular area of myocardium. Long term follow-up demonstrated patency of this conduit, although it improved blood supply to only a very small area of myocardium. This procedure then evolved to another method wherein conduits or grafts, i.e. veins from the legs, are attached surgically from the aorta to native coronary arteries in order to direct blood flow past a more upstream local obstruction and into the native coronary artery. The initial use of the LITA revascularization graft was in 1967, and since that time it has been proven that this graft has the highest patency rate in comparison to vein bypass grafts from the legs.

Angiographic assessment of the left internal thoracic artery is important for many reasons, and particularly important in four clinical settings. First, assessment should be performed prior to the insertion of a device to remove arterial obstruction in the proximal left anterior descending coronary artery. Such assessment should also be performed prior to coronary artery bypass graft surgery involving potential bypass to the left coronary system, i.e., left anterior descending coronary artery, diagonal coronary artery, or circumflex coronary artery. Additionally, angiographic assessment is recommended following coronary artery bypass graft surgery where the LITA was used as a bypass conduit. The fourth setting is when a procedure such as percutaneous transluminal coronary angioplasty of the LITA or LITA-anastomosis or distal area in the vessel beyond the LITA insertion is performed.

Atherosclerotic blockage or stenosis of the very proximal left anterior descending coronary artery may be successfully relieved using the catheter balloon technique of percutaneous transluminal coronary angioplasty (PTCA). During this technique, a guiding catheter is placed in the origin of the left main coronary artery and a wire is placed across the left anterior descending coronary artery stenosis followed by a balloon dilatation catheter in the area of stenosis. However, the proximal location of the left anterior descending coronary artery stenosis carries a much lower success rate than PTCA in any other area of this vessel or any other vessel. Indeed, three-month re-stenosis rates may exceed 50 percent in the proximal left anterior descending coronary artery, in contrast to the middle or distal left anterior descending coronary artery or other coronary vessel where the re-stenosis rate at three months is in the 5 to 8 percent range. Moreover, when rapid acute closure occurs, coronary artery bypass surgery mortality rates exceed those performed in a routine scheduled setting. For these reasons, it has been advocated in proximal left anterior descending coronary artery stenosis that the patient should be offered coronary artery bypass surgery as an alternative.

To help with the decision making process, each patient considered for proximal left anterior descending coronary artery PTCA should have pre-PTCA LITA angiography. This permits assessment of the LITA diameter in comparison with the recipient left anterior descending coronary artery (hereinafter referred to interchangeably as LAD). If the diameters or lumens of the LITA and LAD are perfectly matched, then the patient may be encouraged to choose elective low risk coronary artery bypass surgery as opposed to PTCA of the proximal LAD. However, recognizing a much lower long term patency rate for saphenous vein bypass grafts, if the LITA-LAD diameters are mismatched and a saphenous vein (hereinafter referred to as SVBG) is likely to be the conduit, PTCA may be the preferable procedure for proximal left anterior descending coronary artery stenosis.

Most patients undergoing coronary artery bypass surgery have left coronary system atherosclerosis present in one or all of the left anterior descending (LAD), left ventricular diagonal (branch of the LAD), or the circumflex (CIRC) arteries. Therefore, most patients having this surgery will have a LITA bypass if possible. Pre-surgery left internal thoracic artery arteriography should be performed. Such a procedure will provide an assessment of the patency of the left subclavian artery. The LITA arises from the left subclavian artery and any significant atherosclerosis will compromise the flow to the LITA and eliminate it as an acceptable bypass conduit. Additionally, the diameter of the LITA will be identified in order to compare it with native blocked coronary arteries and decide which vessel(s) would be best suited for the bypass graft. The length of the LITA is also determined by use of arteriography to see which stenosed arteries can be reached with the LITA. If a long LITA has a large distal diameter, the graft may be anastomosed so that the side of the LITA inserts into a side blocked coronary artery (side-to-side anastomosis) and the end of the LITA is inserted into the side of another blocked coronary artery (end-to-side anastomosis).

Side branch visualization of the LITA will permit the surgeon and cardiologist to evaluate pre-operatively the appropriate take down or repositioning of the LITA pedicle. If a very large transverse artery side branch is present, a coronary steal syndrome may result whereby blood flow preferentially goes down the transverse vessel to the neck and shoulder muscles (increased with arm and shoulder exercises), instead of down the LITA to the bypassed coronary artery. The large side branch can be ligated if it is in a position that is surgically accessible. In a significant number of cases, a LITA may be rejected as a surgical conduit if the side branches cannot be ligated, for example, if it lies under the clavicle.

If no significant side branches are present proximally, the dissection to free up the LITA pedicle can be limited to just the distal portion of the pedicle. Limiting surgical manipulation is important since excess manipulation may result in external vascular irritation, foreign body giant cell reaction, or late LITA occlusion. Alternatively, a large distal side branch may be found permitting it to be used as a separate conduit, i.e., the LITA would end in two equal sized branches, each of which could be used as a separate bypass graft.

Atherosclerosis infrequently develops in the left internal thoracic artery, but surgical manipulation of the LITA during coronary artery bypass surgery may lead to external factors causing stenosis or occlusion in the proximal portion of the fragile LITA. Although the site of the post surgical total occlusion of the LITA is, accordingly, in the proximal one-third of the conduit, partial stenosis of the LITA graft is usually at the point where the LITA is surgically attached to the native coronary artery. PTCA of a stenotic LITA, anastomosis, or a more distant native vessel has become a successful therapeutic modality for restoring vascular supply to a grafted coronary artery and avoids repeat bypass surgery.

During the conventional PTCA technique, under local anesthesia in the groin (or brachial area), a 7, 8, or 9 French guiding catheter is inserted percutaneously into either the femoral or brachial artery and advanced over a guidewire into the left subclavian and on into the LITA. The large caliber wire is then removed and a small caliber PTCA wire is inserted through the guiding catheter into the LITA and across the stenosis. A balloon catheter (or other device for removing arterial obstruction) is advanced over the PTCA wire into the area of stenosis and is inflated thus restoring normal blood flow to the area of the heart muscle served by the blocked coronary artery.

The large population of patients undergoing coronary artery bypass graft for left coronary artery system disease requiring LITA grafts, the assessment of LITA for PTCA to the proximal left anterior, and the large number of patients returning for repeat coronary artery bypass surgery, (i.e., one-third of the procedures are in patients whose grafts have closed) necessitate LITA angiography in many patients presently undergoing coronary artery catheterization.

However, certain geriatric and congenital factors play a role in deterring selective catheterization and angiography of the left internal thoracic artery. In a younger adult the left subclavian arises at a gentle angle from the aorta and is easily entered with a guide wire without manipulation. As the abdominal aorta, lower thoracic aorta and aortic arch elongate with age, they eventually displace the left subclavian superiorly, anteriorly, and toward the right thorax. Initially this produces an "S" shaped subclavian artery which ultimately results in a severe acute angulation of the left subclavian artery from the aorta. This process alone makes selective catheterization of the left subclavian artery very difficult. Displacement of the left subclavian artery is a common finding in older patients returning for catheterization eight to ten years after coronary artery bypass surgery. So, any new device or method of catheterization must take into account the anatomic aging subclavian artery displacement factor.

Considerable congenital variation in the origin of the LITA from the left subclavian artery is also noted. Approximately eighty percent of the LITAs arise anteriorly and inferiorly from the left subclavian artery. In this location the origin may be separate or as a common origin with a transverse vessel. Approximately twenty percent of the LITAs arise anteriorly and superiorly, not from the left subclavian, but from the left thyrocervical trunk artery. Also, the LITA may arise variously from 1 to 4 centimeters from the ostium of the left subclavian artery.

During selective catheterization of the LITA, a dissection or tear in the inside lining of the vessel of the subclavian of LITA may occur due to the fragile nature of the vessel. Dissection of the LITA as a graft has resulted in anterior myocardial infarctions.

Recognizing the inherent congenital and geriatric anatomical technical problems with the femoral approach to the LITA, a brachial approach alternative has been suggested in which an ipsolateral brachial insertion of a guiding catheter for LITA angiography was performed. However, this was associated with complications. Three of eight procedures were complicated by ventricular fibrillation, cardiac arrest, LITA spasm, or dissection.

A special left internal thoracic artery catheter to be used by the right brachial approach has been suggested in a prior art publication, but the technique has not received acceptance due to risk to the right cerebrovascular arteries, and physician unfamiliarity with PTCA via the brachial approach.

Using commercially available performed right Judkins coronary catheters, (or slightly more angular distal tip catheters), entry into a LITA from the femoral artery is inconsistently achieved yet may be associated with vessel trauma. Indeed, as the population of patients requiring LITA selective catheterization angiography gets older, the geriatric technical factors will further reduce successful instances of cannulation of this vessel.

A venous injection of contrast with computer digital subtraction angiography of the LITA has also been suggested. The method was proposed because of technical difficulties of catheterization of the LITA, and to improve visualization in patients with subclavian tortuosity or anomalous LITA origins. The digital subtraction angiography method was subsequently extended to an invasive procedure. After a cardiac catheterization the patient is taken to the X-ray department where an aortic injection of contrast was provided followed by digital subtraction angiography. However, poor visualization of the distal LITA and absence of visualization of the bypassed native arteries make the procedure not only an impractical one, but one which fails to meet the criteria established for adequate visualization of the LITA. Also, without selective catheterization, PTCA could not be performed through this technique.

U.S. Pat. No. 4,909,258 suggested use of a catheter with a distal balloon and proximal port similar to that used years ago for dry limb angiography. The procedure involved occluding blood flow to the distal subclavian ancillary artery, identifying the LITA, and then entering the LITA through the side port with a guidewire and apparatus to remove vascular obstruction. The disclosed apparatus will not find usefulness to solve the current problems for several reasons. First, the apparatus will not be able to properly enter the displaced left subclavian. Most of the patients returning for repeat angiography after LITA graft surgery are in the older age group where geriatric changes in the subclavian have already started to occur. Second, the technique requires inflation of a balloon in an otherwise normal subclavian artery just distal to the LITA. It is well known that balloon inflation in a normal artery is considered traumatic. With wire and PTCA manipulation, the balloon may, in itself, produce shear forces sufficient to expose subendothelial tissue and cause thrombogenic trauma leading to the release of tissue factors resulting in stenosis of the vessel. Furthermore, the system described will not offer sufficient support and pushability or ease of advancement of an apparatus over the wire to remove vascular stenosis. An example of this problem occurs when the apparatus is advanced through the balloon catheter over the wire and into an accordionized LITA or area of stenosis, resulting in the entire apparatus prolapsing retrograde proximally into the subclavian.

Accordingly, a safe and reliable method and apparatus to enter the left subclavian artery and successfully cannulate the LITA is needed to provide complete pre-operative, pre-proximal LAD PTCA, and post-coronary artery bypass surgery angiography and angioplasty for either a normal or displaced left subclavian artery. It has been discovered that the normal or displaced left subclavian artery and variably positioned LITA can be consistently, safely, and selectively catheterized using the apparatus and method of this invention.

Another object of the present invention is to selectively simultaneously visualize the left subclavian and LITA artery/graft and its native/bypassed blocked coronary artery without traumatizing the vessels.

Yet another object of the present invention is to provide a strong platform support in order to remove a stenosis in the LITA artery/graft or its bypassed native vessel without catheter manipulation and with continuous blood flow to the heart muscle/myocardium through the side hole and end hole combination of the device of the present invention.

Accordingly, this invention is an apparatus and direct method for simultaneously injecting radiopaque media or contrast into a left subclavian, LITA artery/graft or its bypassed vessels. Preferred catheter characteristics include a soft, deformable short tip; a canted, distal curve on the catheter tip to hook or engage the left subclavian artery; and a series of primary curves to accommodate the varying LITA-subclavian artery combinations, with side ports in the primary curves, and a firm shaft with pushability into the primary curves.

This apparatus is preferably percutaneously inseted into the femoral artery over a guidewire and advanced to the ascending aorta and then into the left subclavian and left internal thoracic artery. Radiopaque media is then injected and exits through the side ports to the left subclavian and through the distal tip port to visualize a LITA artery/graft, its branches, and bypassed coronary arteries.

The present invention is also an apparatus and method for enlarging the LITA/graft, its anastomosis, or the native vessels served by the LITA/graft. A guidewire is directed past the side ports and exits through a distal port into the LITA/graft and into a native bypassed vessel. A continuous supply of blood flows through the left subclavian artery, into the side holes, down the catheter lumen and into the LITA graft, permitting continuous profusion of myocardium in the distribution of the bypassed vessel. An apparatus to remove arterial blockage is then advanced over the guidewire in the area of obstruction (balloon catheter, atherectomy device, laser catheter, stints, impregnable chemicals, or other means). It is, therefore, yet another object of this invention and apparatus to selectively cannulate the LITA in order to provide an apparatus to remove arterial obstruction while perfusing the distal vessel continuously with fresh oxygenated blood.

Objects and advantages of the present invention in achieving these and other goals will become apparent from the following descriptions, taken in connection with the accompanying drawings, wherein are set forth by way of illustration and example certain embodiments of the present invention.

SUMMARY OF THE INVENTION

The present invention involves placing a catheter (tube) with a canted, deformable, atraumatic tip, and end port, and a curved firm shaft with side ports, into the origin of a normal or displaced left subclavian artery and advancing it over a guidewire into the origin of the LITA through a femoral artery puncture site. The soft, gentle, canted, deformable, short tip of the catheter permits atraumatic injection of radiopaque contrast material into the entire LITA and all of its branches. In the subclavian the curved shaft with side ports, just proximal to the LITA, permit non-traumatic firm catheter tip support while contrast exists the side ports of the catheter permitting simultaneous visualization of the left subclavian and LITA. With the invented apparatus in this same position, other equipment (PTCA balloon, laser, balloon, atherectomy, stent, or impregnable chemicals) to remove or prevent vascular stenosis, may be inserted into the LITA, its anastomosis or a blocked native bypassed coronary artery. The canted, short, non-traumatic deformable tip, and curved firm reinforced shaft insure entry into the left subclavian which is frequently markedly displaced to the right. This is the first common difficult step encountered in selective catheterization of the LITA. A curved catheter shaft lying against the arterial wall opposite to the LITA origin adds significant catheter tip support and safely increases pushability of the inserted device over the guidewire. The side ports permit continuous blood flow to the LITA and its bypass vessels during device insertion and manipulation by blood entering the side ports from the left subclavian artery, coursing down the catheter lumen to the deformable end port and into the LITA.

It has been discovered that the invented apparatus successfully overcomes six major obstacles to safe consistent selective catheterization of the left subclavian and LITA. These include the following: (1) the difficult challenge of selectively catheterizing the inconspicuous or occult but commonly displaced geriatric left subclavian artery; (2) selective catheterization of the LITA in regard to its varying congenital origin from the left subclavian or left thyrocervical trunk artery; (3) the visualization of very large proximal origin LITA transverse side branch, left transverse Coli or left suprascapular artery; (4) catheter tip manipulation and contrast injection without trauma or dissection to the left subclavian artery or LITA/graft; (5) simultaneous left subclavian and LITA radiopaque visualization; and (6) strong, safe platform for the LITA catheter in order to advance an apparatus to remove/prevent arterial stenosis while providing continuous blood supply to the bypassed artery.

The drawings constitute a part of this specification and include exemplary embodiments with the present invention, while illustrating various objects and features thereof. It will be understood that in some instances relative material thicknesses and relative component sizes and dimensions may be shown exaggerated, to facilitate an understanding of the invention.

As required, detailed embodiments of the present invention are disclosed herein. It is to be understood, however, that the disclosed embodiments are merely exemplary of the invention, which may be embodied in various forms. Therefore, specific structural and functional details disclosed herein are not to be interpreted as limiting, but rather as a basis for the claims and as a representative basis for teaching one skilled in the art to variously employ the present invention in virtually any appropriately detailed system or structure.

Figure 1:
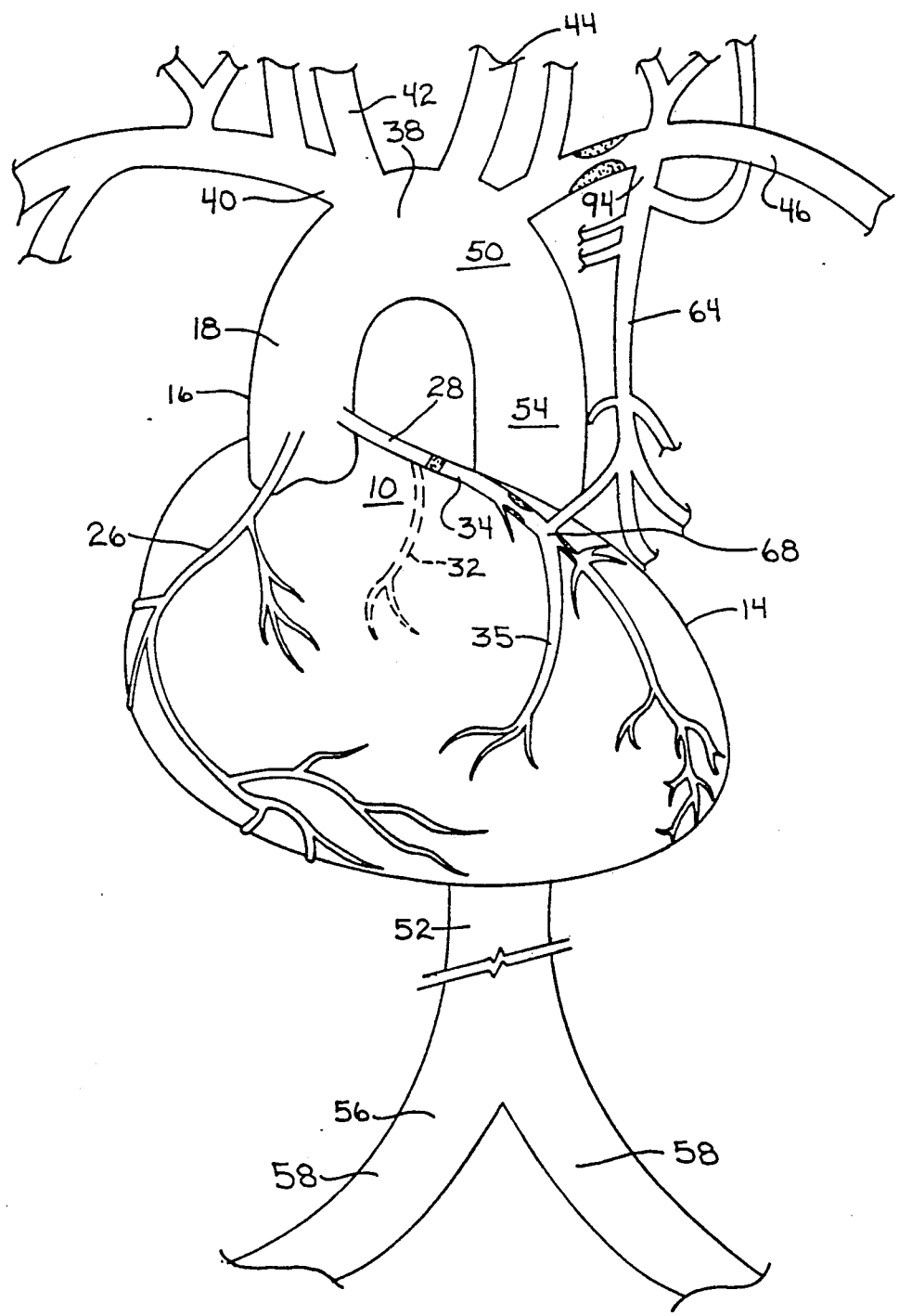
FIG. 1 is a side elevational diagram of a heart, including the ascending aorta, aortic arch, descending aorta, and abdominal aorta depicting the origin of the arch vessels including the left subclavian artery and the left internal thoracic artery after surgical anastomosis to the left anterior descending coronary artery with total occlusion of the left anterior descending coronary followed by partial stenoses before and after the LITA anastomosis.

Referring to FIG. 1, oxygenated blood exits the left lower heart pump or left ventricle 10 of heart 14 and enters a large trunk artery, the aorta 16, more specifically, the ascending aorta 18. Since the contracting heart muscle cells or myocardium forming the heart chambers cannot exchange oxygen and materials because of the endocardium or cellophane-like lining, the first two arteries arising from ascending aorta 18, the right coronary artery 26 and the left main coronary artery 28 provide conduits to the heart muscle cells. Left main coronary artery 28 divides or bifurcates into the circumflex coronary artery 32 and the left anterior descending coronary artery 34 herein referred to interchangeably as LAD 34. LAD 34 has several large branches called the left ventricular diagonals 35. Subsequent arteries arising from the aortic arch 38 include the right inominate 40, right carotid 42, left carotid 44, and finally the left subclavian artery 46. Thereafter, the descending aorta 50 and the abdominal aorta 52 continue through the abdomen where they bifurcate into the iliac 56 and finally the femoral arteries 58 at the groin area.

When LAD 34 or left ventricular diagonal 35 branch of LAD 34, become partially stenosed, or totally occluded, transient or permanent decrease in blood supply (ischemia) to the heart muscle cells may occur. This results in transient or permanent reduction in heart pump, i.e. left ventricular 10, contractility.

To restore blood supply to transient ischemic myocardium, the distal left internal thoracic artery may be dissected free of the chest wall and surgically attached or anastomosed to the downstream blocked coronary artery. Thus, LITA 64 is used as a conduit to carry blood from aortic arch 38 to left subclavian 46, to the LITA graft 68, and into the vessel beyond the obstruction.

Figure 2A:
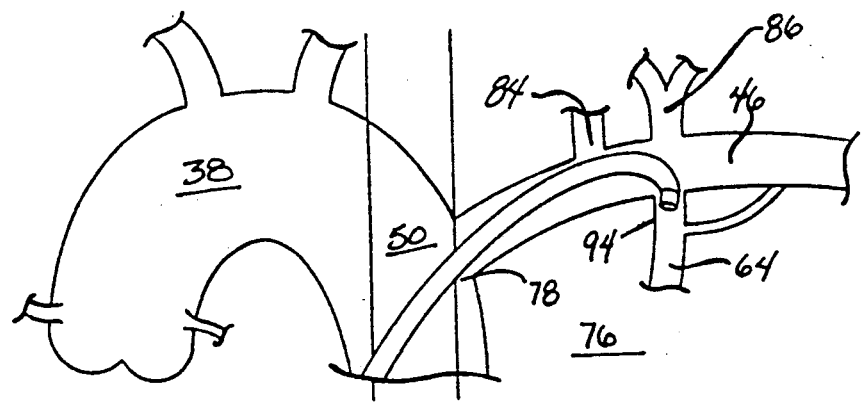
FIG. 2A is a cross sectional diagram of a normal young aortic arch and its relationship to the origin of the left subclavian artery.
Figure 2B:
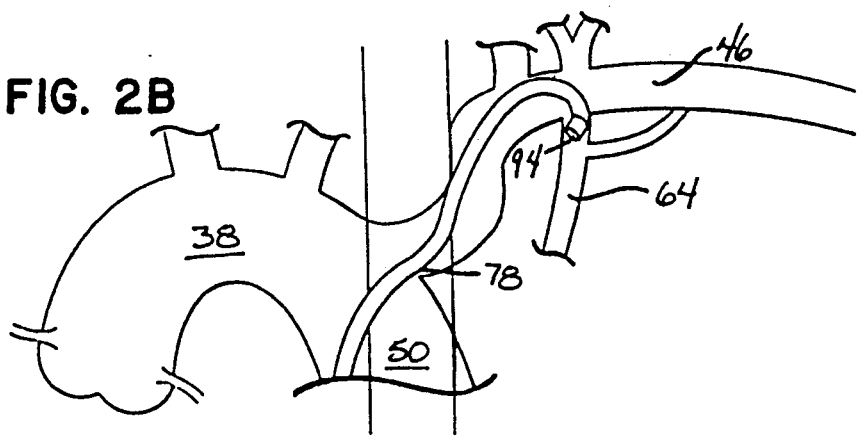
FIG. 2B is a cross sectional diagram of the aortic arch depicted in FIG. 2A, but showing geriatric growth patterns as the aorta progressively displaces the origin of the left subclavian artery into the right thorax, producing an "S" shaped left subclavian.
Figure 2C:
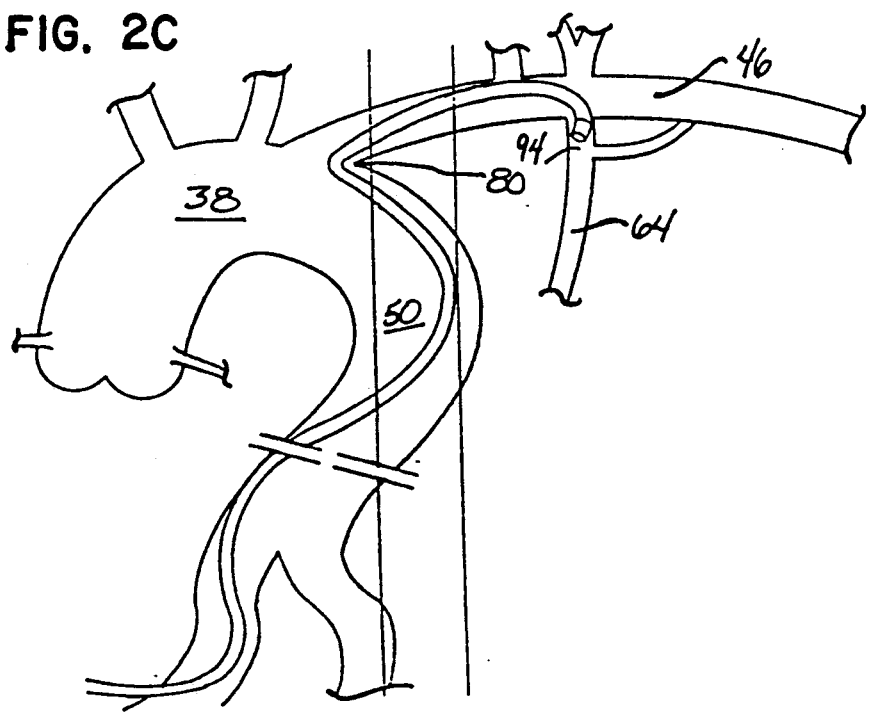
FIG. 2C is a cross sectional diagram of the aortic arch depicted in FIG. 2B, but showing further geriatric growth wherein severe angulation of the left subclavian artery has occurred relative to the geriatrically displaced aortic arch.

Left subclavian artery 46 springs from aortic arch 38 as its last major branch before the aorta descends into the abdomen as abdominal aorta 52. In the first five decades of life, left subclavian artery 46 is easily entered with a guidewire 74 inserted percutaneously into femoral artery 58, as is shown in FIG. 2A. In this age group left subclavian artery 46 is almost in a direct line from descending aorta 50 and abdominal aorta 52. By the sixth decade, at a time when atherosclerotic disease/bypass becomes more frequent, the iliac artery 56, the abdominal aorta 52, and the descending thoracic aorta 54 dilate, elongate, and accordionize. As a result of these geriatric growth patterns and the accordionization of the distal abdominal aorta 52, aorta arch 38 starts to shift toward the right thorax 76 and drags with it the origin 78 of left subclavian artery 46. Initially, displaced left subclavian artery 46 produces an "S" shaped deformity in left subclavian 46. Thereafter, with continued arch dilation and displacement toward right thorax 76, an acute angle 80 is formed by left subclavian origin 78 and aortic arch 38. Recognizing the significance of these progressive geriatric aortic vascular changes was quite significant in discovering the apparatus disclosed in this invention, for which there is no other known catheter designed to properly accommodate such changes.

Figure 3A:
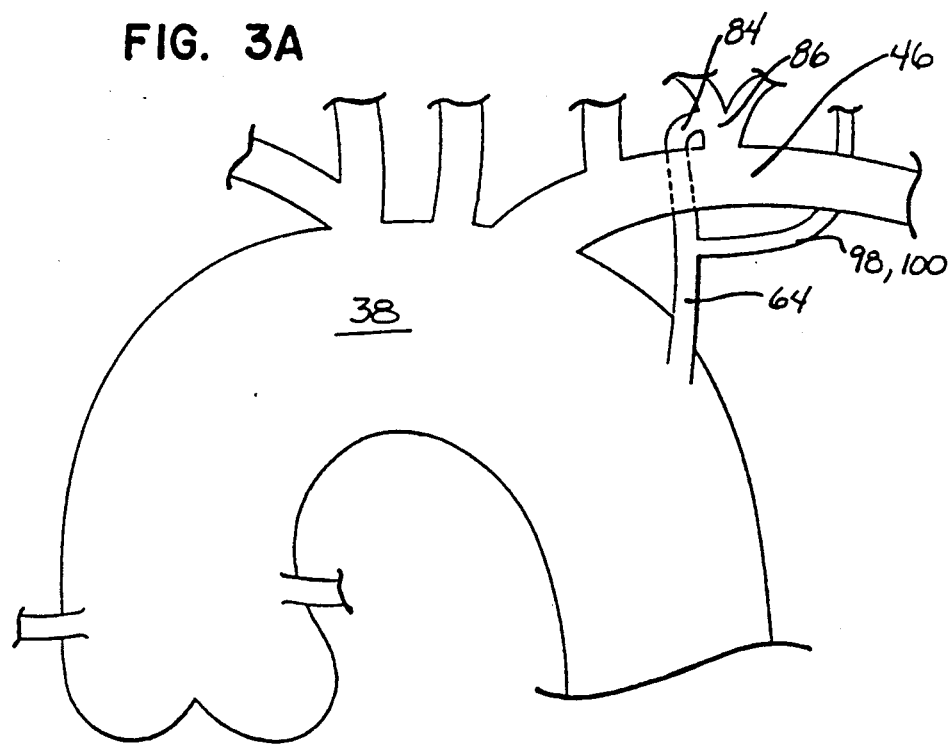
FIG. 3A is a cross sectional diagram depicting the less common origin of the LITA from the superior/anterior location arising not from the left subclavian, but from the left thyrocervical trunk.
Figure 3B:
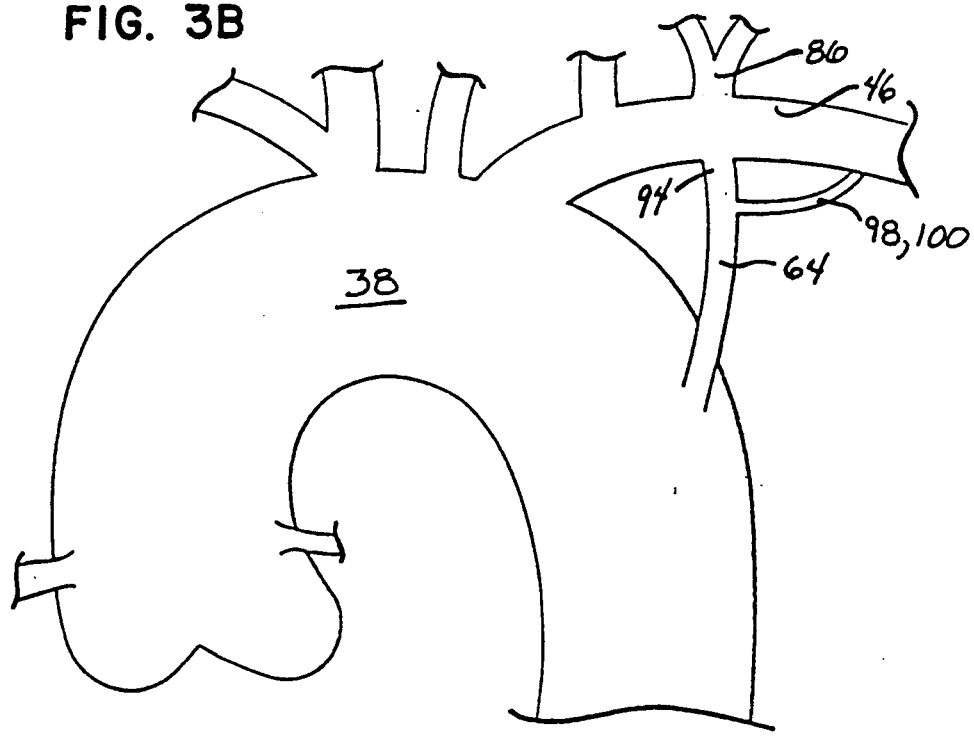
FIG. 3B is a cross sectional diagram of the arch of the aorta and the left subclavian emphasizing the common origin of the LITA from the anterior/inferior surface of the left subclavian artery.
Figure 4A:
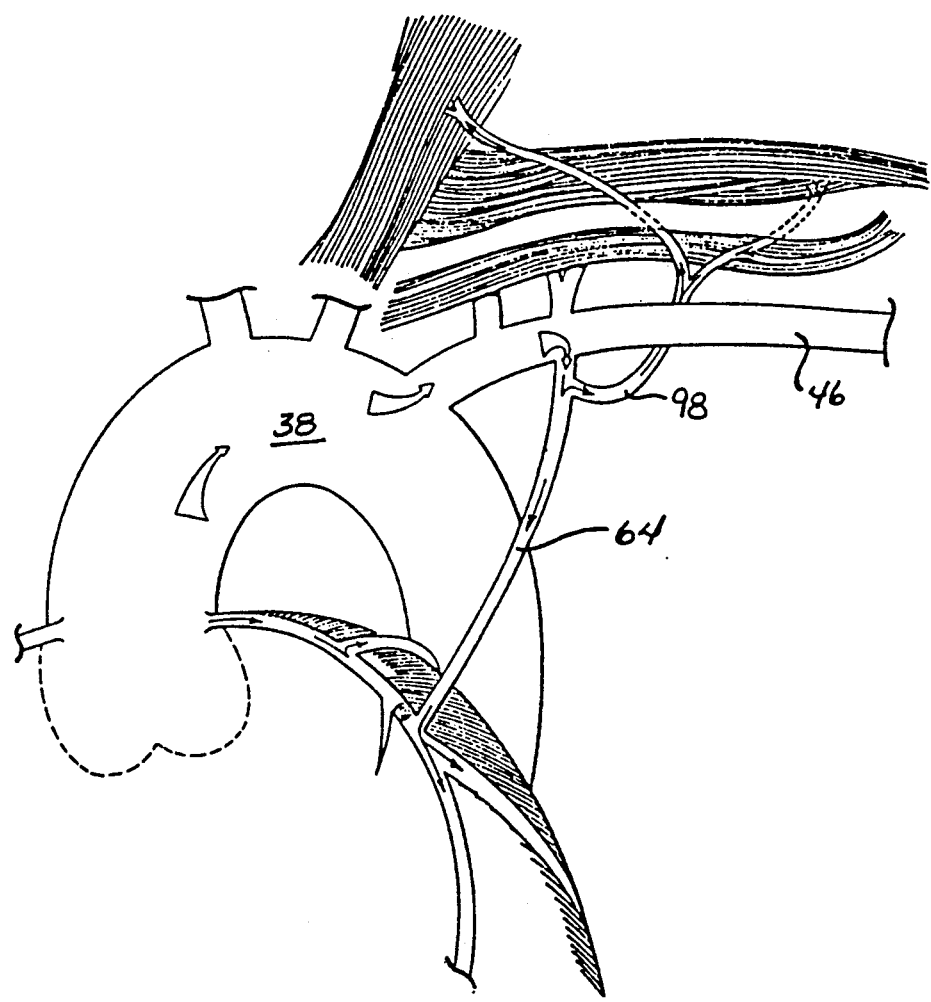
FIG. 4A is a cross sectional diagram demonstrating the presence of an unrecognized large supra scapular artery branch of the left internal thoracic artery producing a coronary steal syndrome from the LITA anastomosed to the LAD.
Figure 4B:
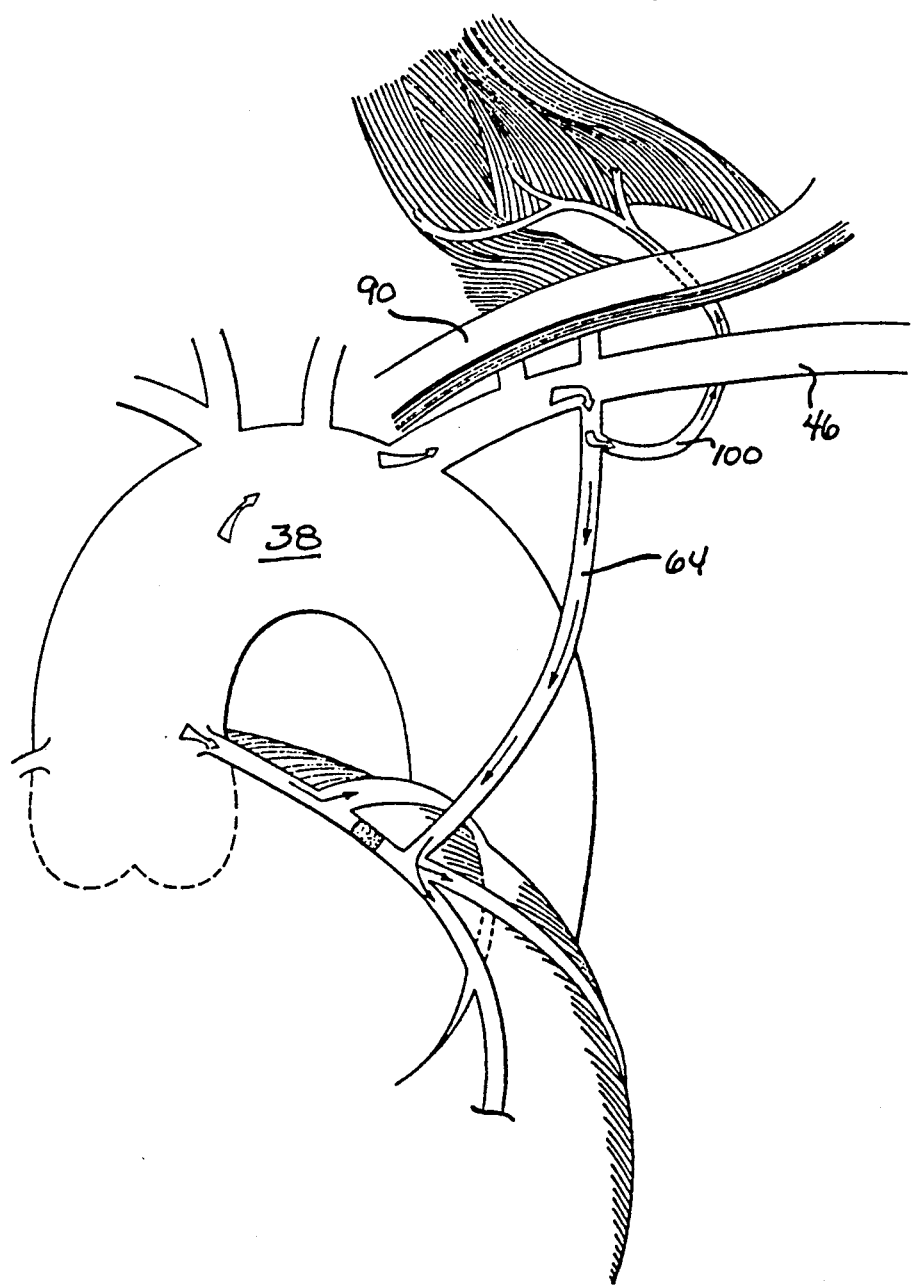
FIG. 4B is a cross sectional diagram depicting a large transverse cervical artery arising from the proximal LITA producing a coronary steal syndrome from the distal LITA anastomosed to the LAD.
Figure 5:
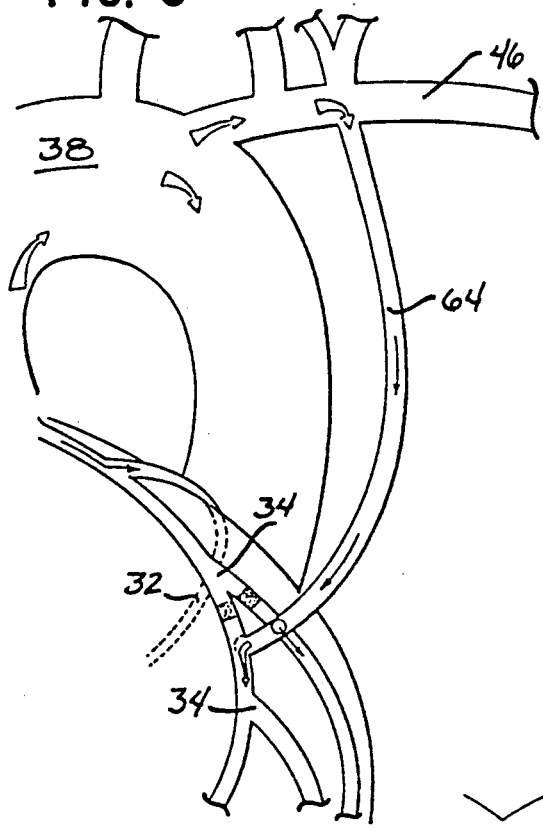
FIG. 5 is a cross sectional diagram demonstrating the LITA used to bypass two blocked coronary arteries using side-to-side and end-to-side surgical anastomoses.
Figure 6:
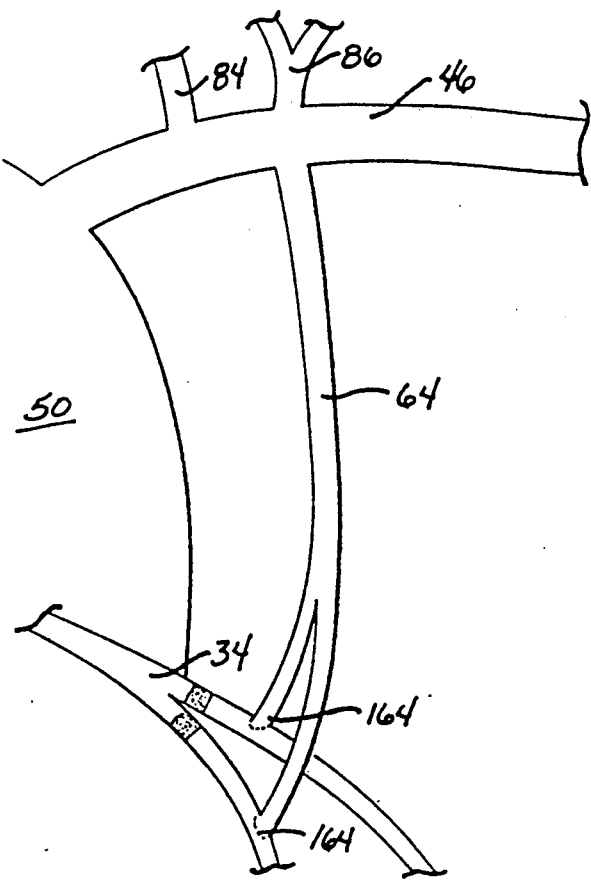
FIG. 6 is a cross sectional diagram of the LITA used as a surgical graft using two distal branches of the LITA for two separate end-to-side anastomoses to two native blocked coronary arteries.

Left subclavian artery 46 provides left vertebral artery 84, serving the back of the brain and the spinal cord, the left thyrocervical trunk artery 86, serving the neck and upper shoulder muscles and skin and LITA 64. The left internal thoracic (mammary) artery 64 springs from the area behind the collar bone 90 on the anterior-inferior surface of left subclavian artery 46 in about 80 percent of individuals, as illustrated in FIG. 3B. However, in about 20 percent of individuals, the LITA arises from left thyrocervical trunk artery 86. This latter anterior-superior location of LITA from left thyrocervical trunk artery 86 is not obvious, but is predictably present when LITA 64 does not arise from left subclavian 46 in its more common anterior-inferior location. Due to these congenital and geriatric vascular growth patterns, the distance between the origin of left subclavian 46 from aorta 16, and the distance of LITA 64 from left subclavian 46 may vary by 1 to 4 centimeters. Recognizing the non-obvious import of these common congenital and geriatric variations of LITA 64 was important in designing and discovering the apparatus and method of this invention.

The very proximal portion 94 of LITA 64 may give origin to a large transverse branch artery, i.e. left supra scapular artery/left transverse scapular artery 98, or the left transverse Coli/left transverse cervical artery 100. When LITA is used as a bypass conduit and there was a pre-operative unidentified large supra scapular or transverse Coli artery, then a coronary steal syndrome may develop. In the postsurgical LITA-LAD bypass setting, exercise initiated increased blood flow to the left neck, shoulder, and back muscles preferentially steals blood out of the proximal LITA and into the supra scapular or transverse Coli artery, thus depriving the LITA-LAD system of blood supply. This may then result in myocardial ischemia reproducing the exact events which initially led to LITA-LAD bypass in the first place. However, if pre-operative angiography identifies this anatomy, the LITA may be properly rejected as a possible conduit and alternative therapeutic choices may be explored. Also, absence of significant sized LITA side branches may permit the cardiac surgeon to limit the dissection and reduce trauma to the LITA in freeing it from the chest wall. Further, the length, diameter, and size of the very distal LITA branches determines if the vessel may be used as a side-to-side anastomosis or an upside down "Y" anastomosis.

Accordingly, the injection of contrast to provide radiopaque visualization of the left subclavian, LITA artery/graft, and distal bypass vasculature provides information for critical pre-operative and post-operative decision making. In the pre-operative setting, the visualization demonstrates the presence or absence of stenosis of the left subclavian artery. If such stenosis is present, it will preclude use of LITA as a conduit. The visualization also reveals the presence of a proximal large transverse vessel that could result in a post-operative coronary steal syndrome, as discussed hereinabove. Information is also revealed through visualization regarding the LITA diameter, length, and size of distal vessel and therefor the possibility of bypassing to several native blocked coronary arteries rather than to only a single vessel.

In the post-operative setting, the presence or absence of left subclavian artery stenosis is determined through visualization. Such stenosis, if present, would be a possible cause of reduction of blood supply to the LITA and resulting myocardial ischemia. The patency of the LITA graft is also determinable. Although atherosclerosis hardly ever develops, inflammatory total occlusion or partial stenosis may occur at the most superior surgical dissection site. Patency of the LITA-coronary anastomosis is observable, as well as the structural integrity of the bypassed coronary artery. Further, the device provides a support platform for insertion of an apparatus or chemical to remove arterial plaque.

Accordingly, the present invention takes into consideration the unobvious geriatric and congenital variations of the left subclavian, and the left internal thoracic artery. The invention also provides an apparatus and a method to more safely, effectively, selectively catheterize the LITA and the left subclavian artery, visualize them simultaneously, and provide a strong, safe support platform in order to accomplish insertion of interventional therapeutic apparatus to remove and/or prevent arterial obstruction.

Referring to FIGS. 7A-7E, the apparatus of the present invention is disclosed comprising a catheter 104 having a single proximal end port 106 and hub 108 for radiopaque contrast injection or interventional apparatus insertion. Catheter 104 has a single continuous lumen 112, a single distal end port 114 (or ports) for exit of contrast and interventional apparatus into the LITA, and a series of side ports 118 in a generally curved portion 122 (and/or sub-portions) of the catheter shaft 124 constructed and arranged for permitting continuous blood flow during LITA cannulization via the left subclavian artery into the side ports. The blood then flows through catheter lumen 112 and exits through single distal end port 114 into the LITA.

Figure 8A:
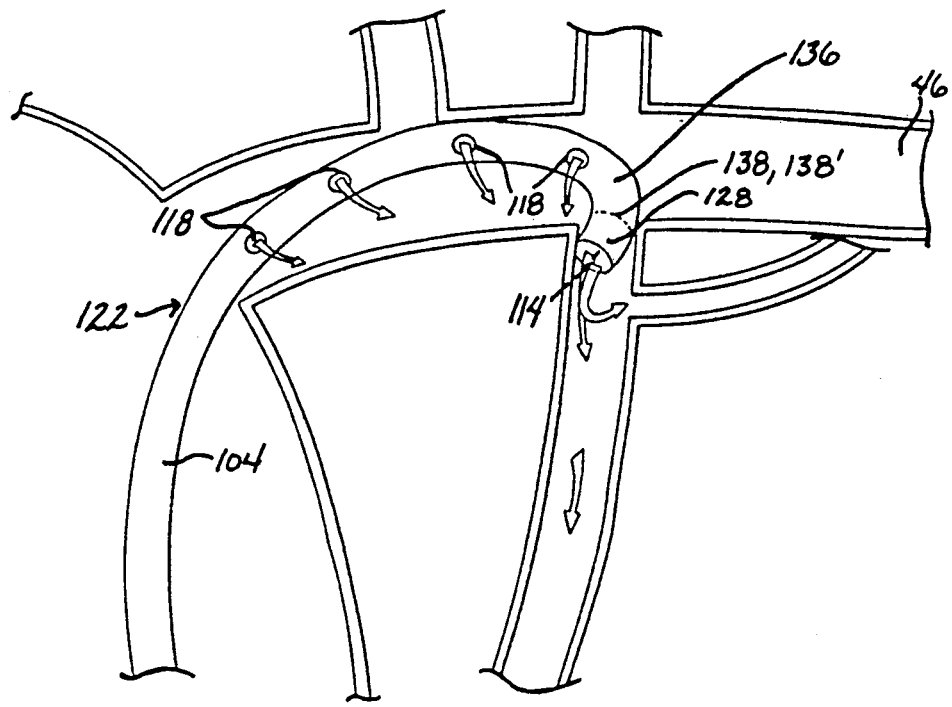
FIG. 8A is a cross sectional diagram and a plain view of the apparatus of the present invention inserted into the left subclavian and selectively into the LITA demonstrating the importance of the side ports into the left subclavian and the end port with soft tip into the LITA for simultaneous visualization of the left subclavian and LITA without traumatic injury to the vessels.
Figure 8B:
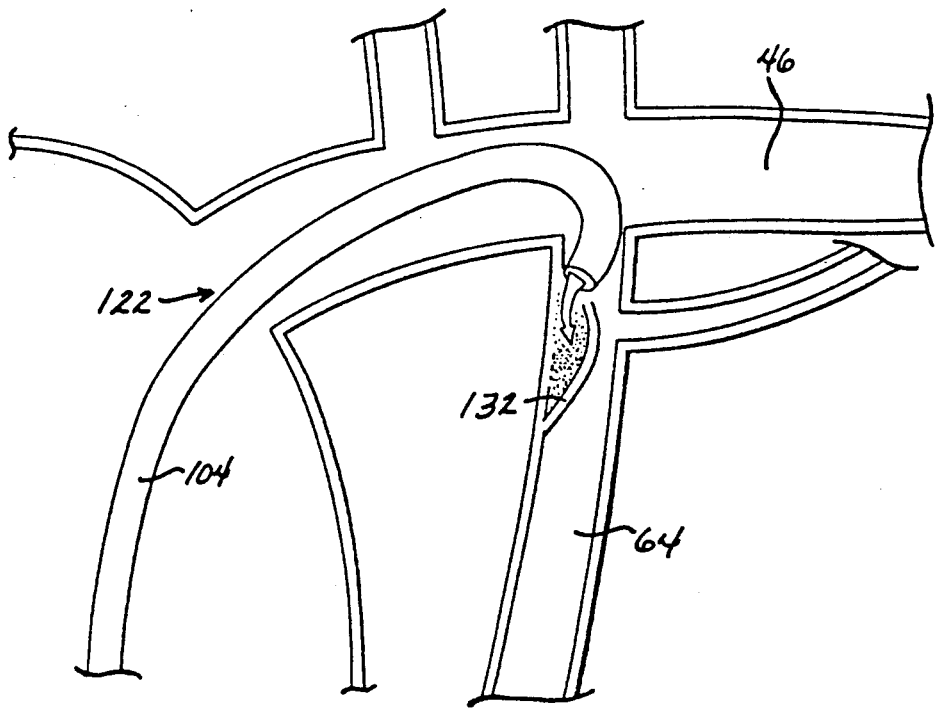
FIG. 8B is a cross sectional diagram of the left subclavian and LITA and plan view of the apparatus of the present invention but without the benefit of the side ports and the soft tip, resulting in all of the force of the contrast injection being exerted on the distal tip and resulting in a tear in the internal lining of the LITA producing a contrast and blood injection into the LITA wall thereby producing a dissecting thrombus and eventually occlusion of the LITA.
Figure 8C:
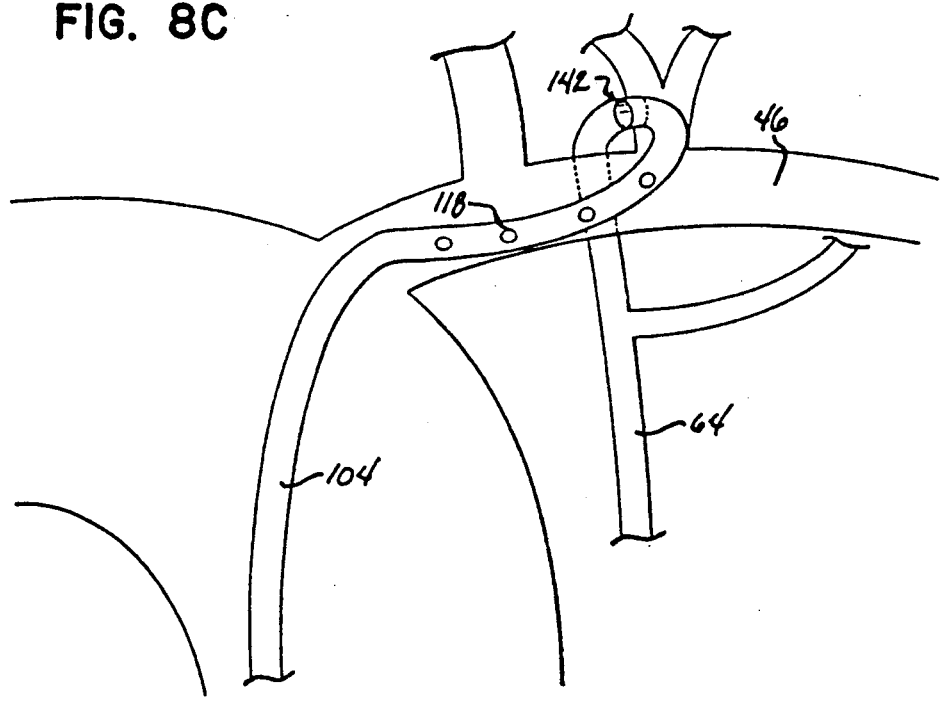
FIG. 8C is a cross sectional diagram of the arch of the aorta, left subclavian artery, and the LITA arising anteriorly-superiorly and medially from the left thyrocervical trunk. The catheter is positioned in the LITA emphasizing the importance of curve "B" and the soft tip provided in order to adapt to the consistent internal angle produced by the origin of the left thyrocervical trunk from the left subclavian artery.
Figure 8D:
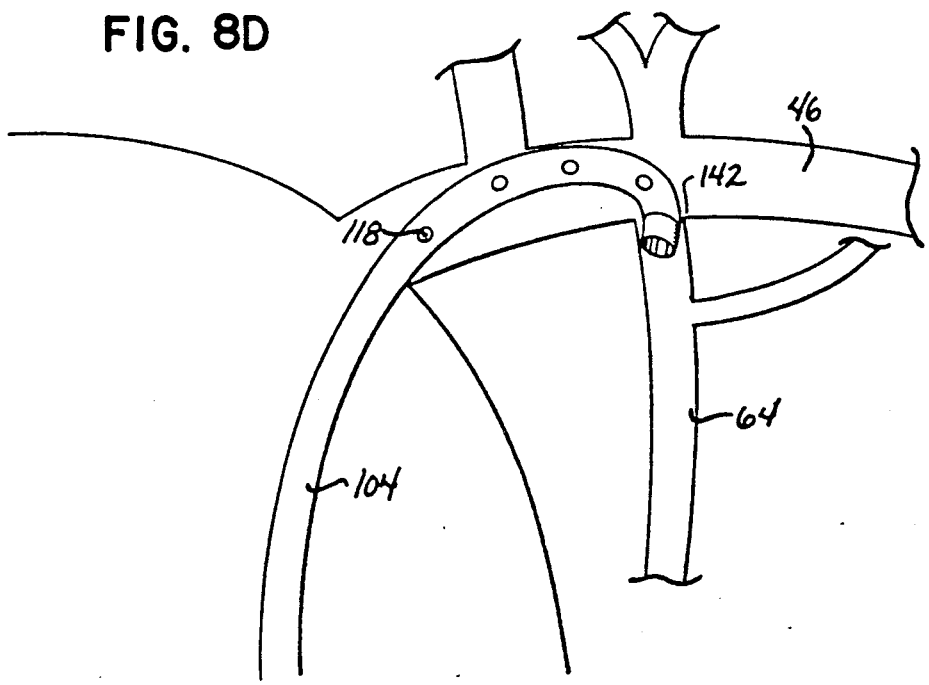
FIG. 8D is a cross sectional diagram of the left subclavian artery and the anterior-inferior location of the LITA from the left subclavian artery. The importance of curve "B" in permitting the distal catheter tip to adapt to the consistent internal angle created by the left subclavian and the LITA is particularly depicted.
Figure 9:
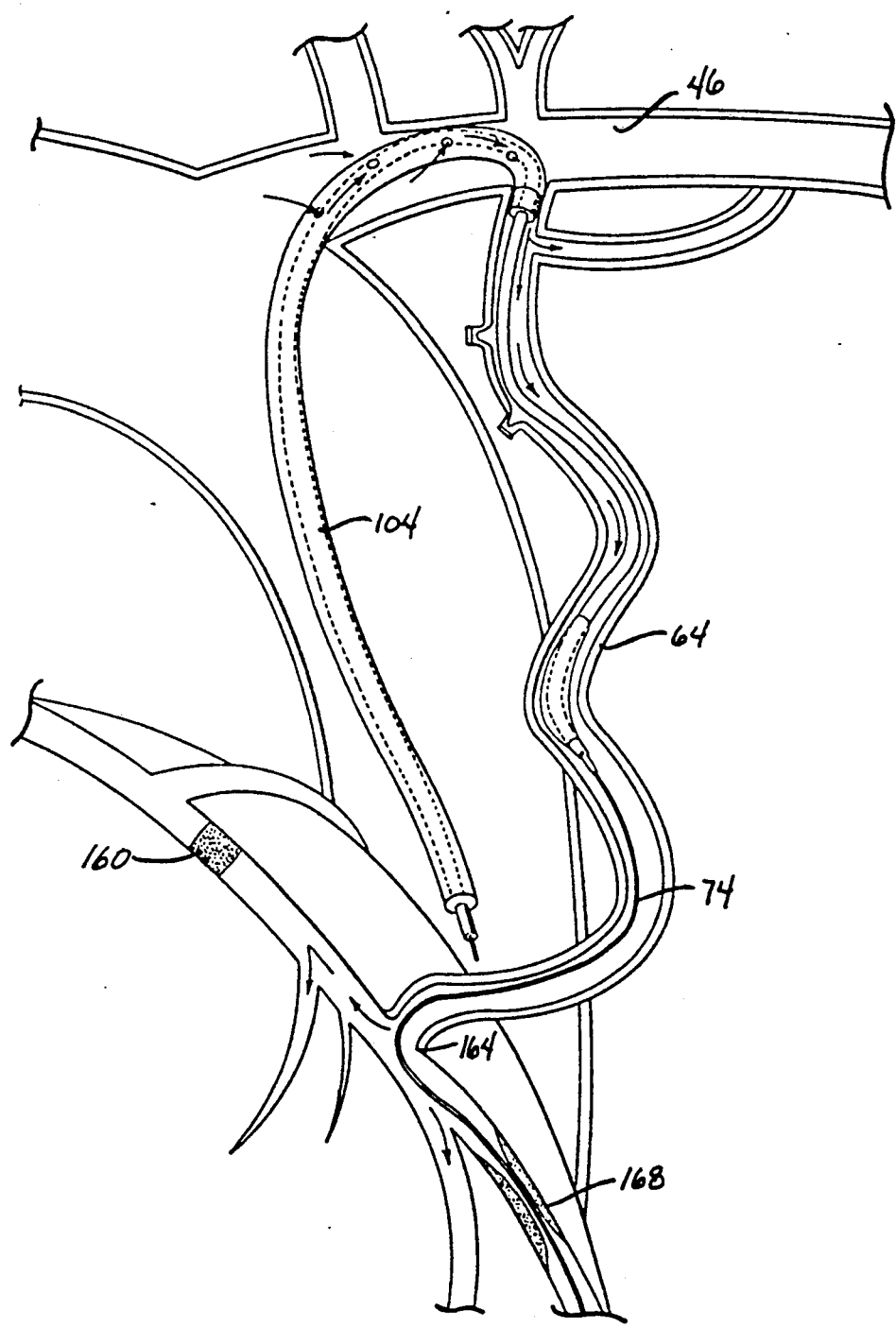
FIG. 9 is a cross sectional diagram of the apparatus of the present invention and PTCA balloon wire apparatus with the wire positioned across the partial stenosis and LAD beyond the LITA graft anastomosis. The LITA graft is very accordionized, and as the balloon is advanced over the wire, significant resistance and drag is produced with a tendency to displace the tip of the invented catheter apparatus into the left subclavian. These forces are counteracted by the catheter shaft opposite the LITA origin lying against the left subclavian arterial wall counteracting the forces trying to displace the catheter tip and offering maximum pushability of PTCA apparatus through the invented catheter apparatus.

In FIG. 8A, the present invention is embodied with side ports 118 and hinged deformable soft tip 128. In FIG. 8B, the present invention is embodied without the additional benefit of side ports 118 and without hinged deformable soft tip 128. In FIG. 8B, all the power applied with the hand injection of contrast to catheter lumen 112 is delivered to distal end port 114. If the catheter tip is not perfectly aligned with lumen 112 of the LITA, then injection of contrast may result in a tear of artery wall 132 and subsequent contrast and blood will develop between the linings of arterial wall 132 as a dissecting thrombus. This will often lead to occlusion of the LITA lumen 112. With side ports 118, such as shown in FIGS. 8A, 8C, 8D, and a hinged deformable soft tip 128, the pressure of the contrast injection is dissipated through side ports 118 into left subclavian 46, and through end port 114, into the LITA (preventing injury to the LITA), and visualizing the left subclavian.

Figure 7A:
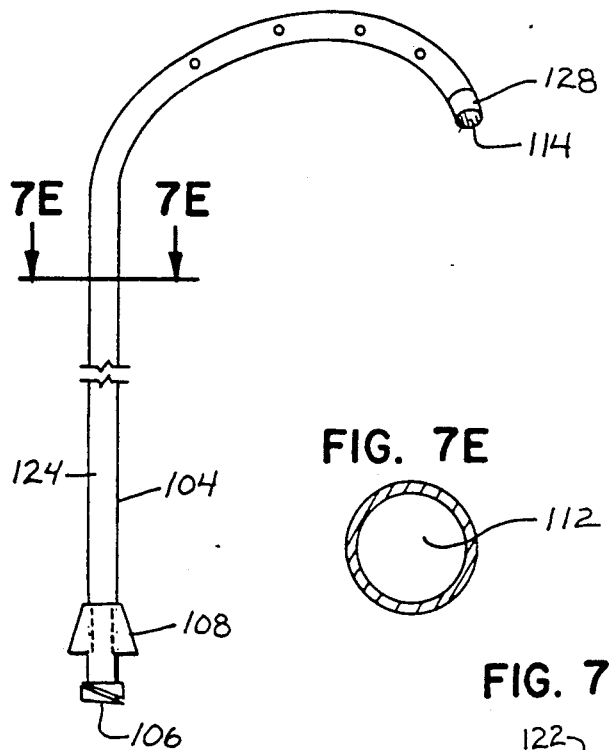
FIG. 7A is a plan view of the apparatus of the present invention depicting the distal and proximal end ports, side holes in the shaft, and soft canted deformable tip with a single lumen throughout the entire shaft.
Figure 7E:
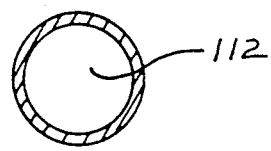
FIG. 7E is a sectional view of catheter lumen taken generally along line 7E—7E of FIG. 7A.
Figure 7B:
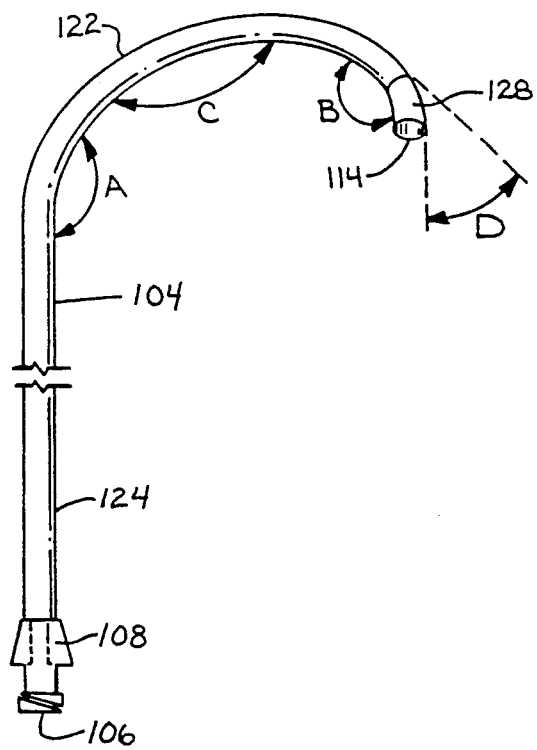
FIG. 7B is a plan view of the apparatus of the present invention demonstrating the four characteristic curves including curve "A" which marks the entry of the catheter shaft from the aorta into the subclavian; curve "C" with the side ports in place; curve "B" the final in-plane curve making entry into the LITA from the subclavian or thyrocervical trunk possible; and the out-of-plane canted curve "D" in order to hook the displaced subclavian artery.
Figure 7D:
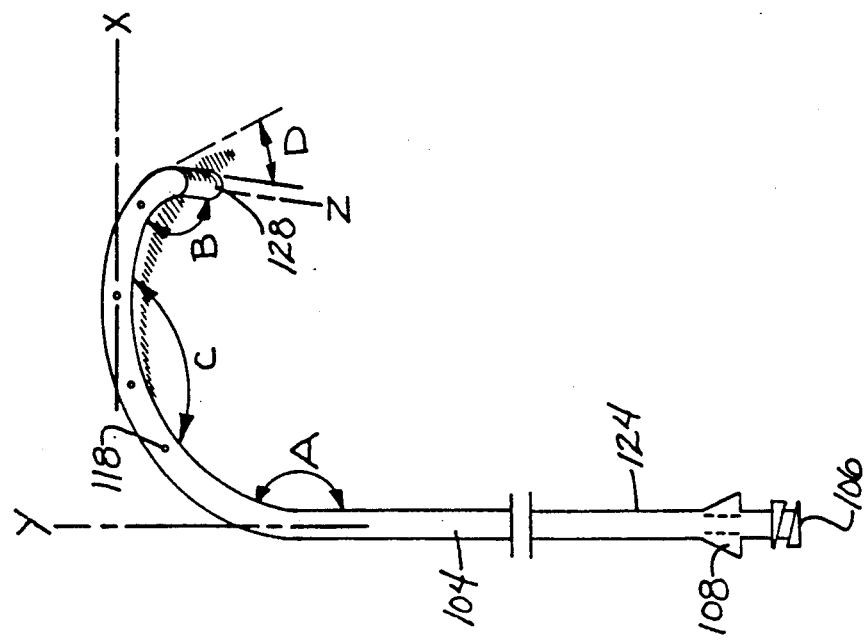
FIG. 7D is a plan view of the catheter illustrating yet another alternative configuration of curve "D."
Figure 7C:
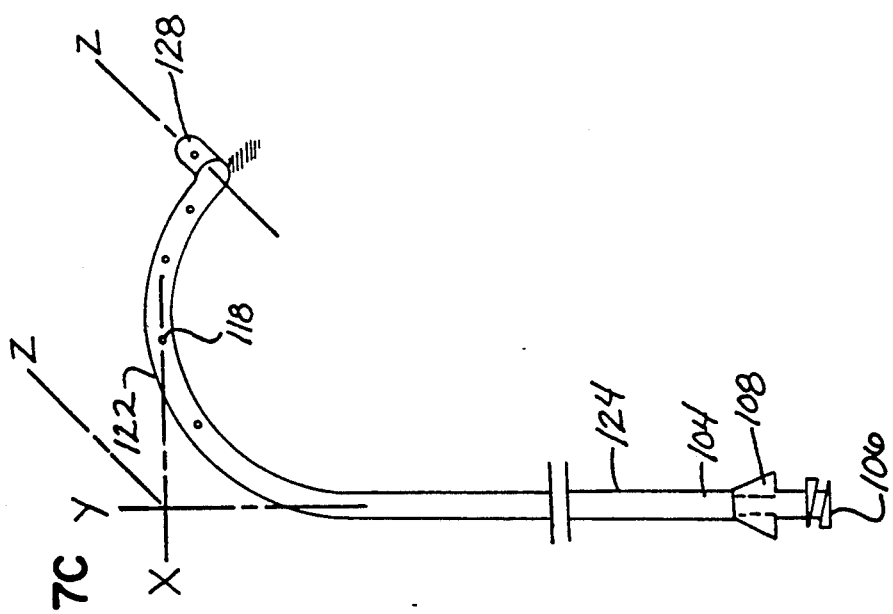
FIG. 7C is a plan view of the catheter illustrating an alternative configuration of out of plane curve "D."
Figure 7F:
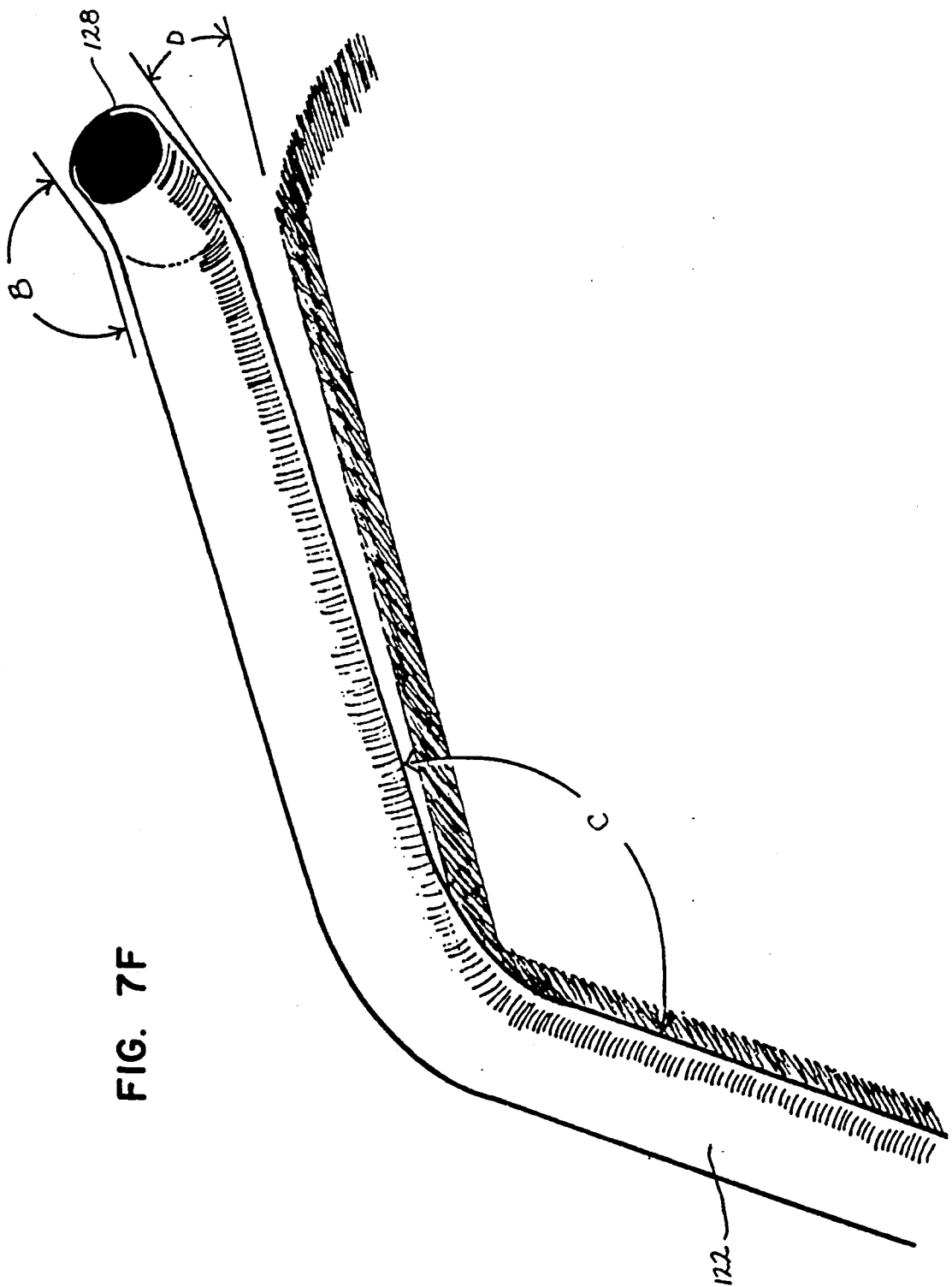
Figure 7G:
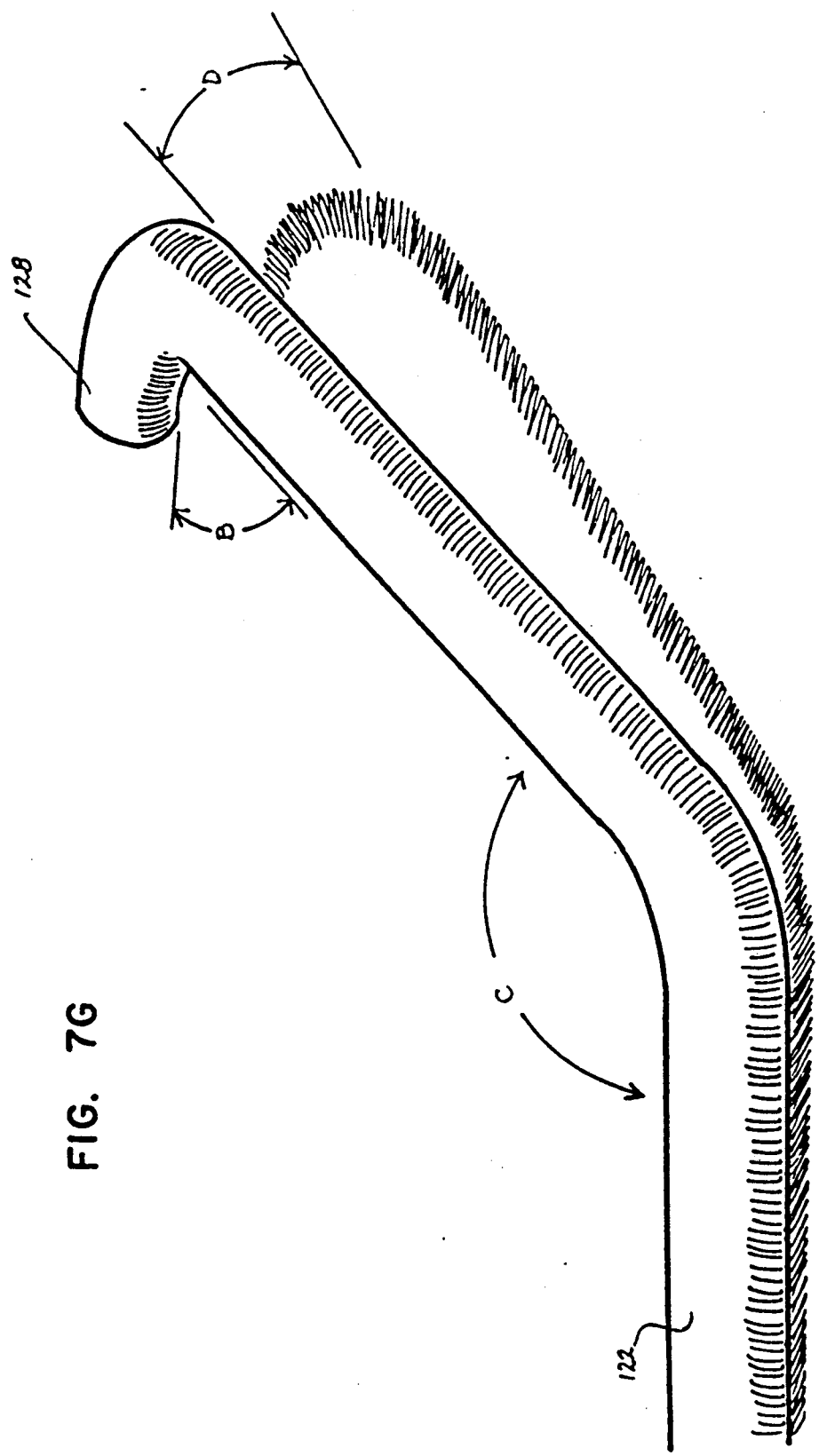

In large part to achieve the above objectives, it has been discovered that the distal catheter shaft, generally depicted at 136, preferably uses a plurality, and most preferably four specific curves, as shown in FIGS. 7B and 7D to meet the demands placed on the apparatus. Curve "B" is designed to comply with the natural and consistent internal angle of LITA 64 from left thyrocervical trunk 86 found in 20 percent of individuals.

Curve "D" is an out-of-plane cant placed on distal catheter tip 138 to engage or hook displaced left subclavian artery 46, and to facilitate entry into the anterior-inferior or superior-anterior origin 142 of LITA 64. This out-of-plane cant in a distal catheter curve will take several, and optimally three, configurations for different shaped subclavian-LITA origins, shown in exemplary configurations of FIGS. 7A, 7C, and 7D, and may comprise curve radii lengths of between 5 mm and 25 mm, although a more preferable range is 8-20 mm.

Curve "C", also shown in FIGS. 7B and 7D, is a gentle curve placed in catheter shaft 124 in order to position the firm shaft against the subclavian arterial wall 132 opposite the LITA or RITA (right internal thoracic artery) origin 142. It has been discovered that this curve "C" permits the operator to have maximum pushability with an intervention apparatus as it is advanced over the PTCA wire. With an accordionized mammary artery, which is common postoperatively, considerable drag is offered as the intervention apparatus is advanced over the wire, and there is a great tendency to displace the guiding catheter tip outward into the subclavian. With the apparatus of this invention, the forces of resistance that try to displace distal catheter tip 138, from the LITA, are easily counteracted by catheter shaft 124, i.e., that portion of shaft 124 comprising curve C lying against the arterial wall 132 opposite the LITA or RITA origin 142.

Figure 10A:
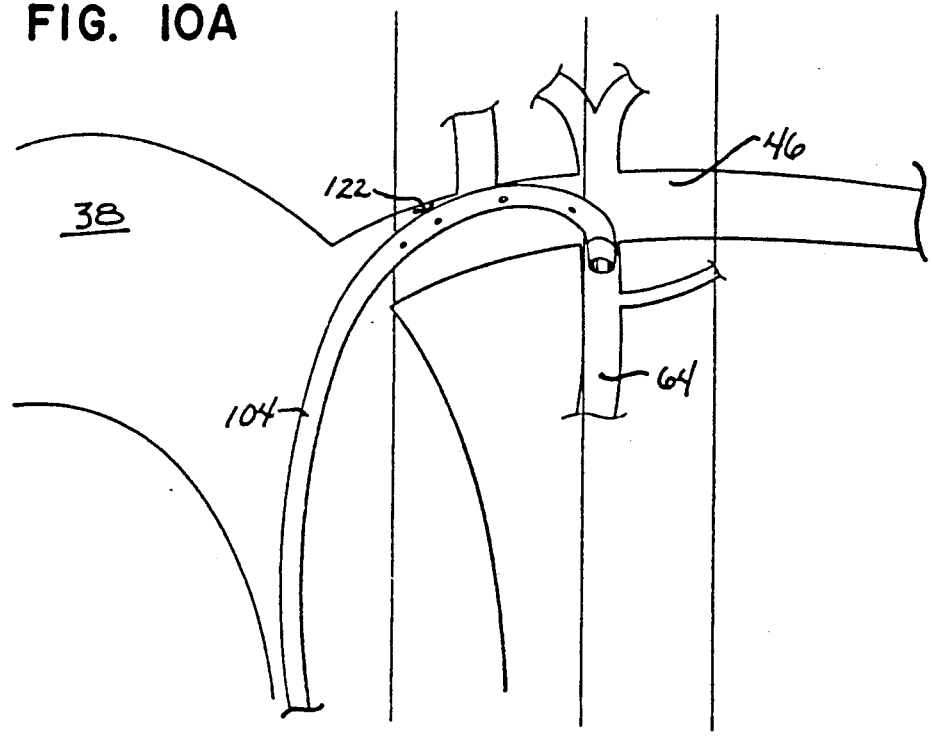
FIG. 10A is a cross sectional diagram of the left subclavian and LITA showing a certain distance of the LITA from the aorta/left subclavian bifurcation, necessitating a series of catheter lengths to accommodate varying distances.
Figure 10B:
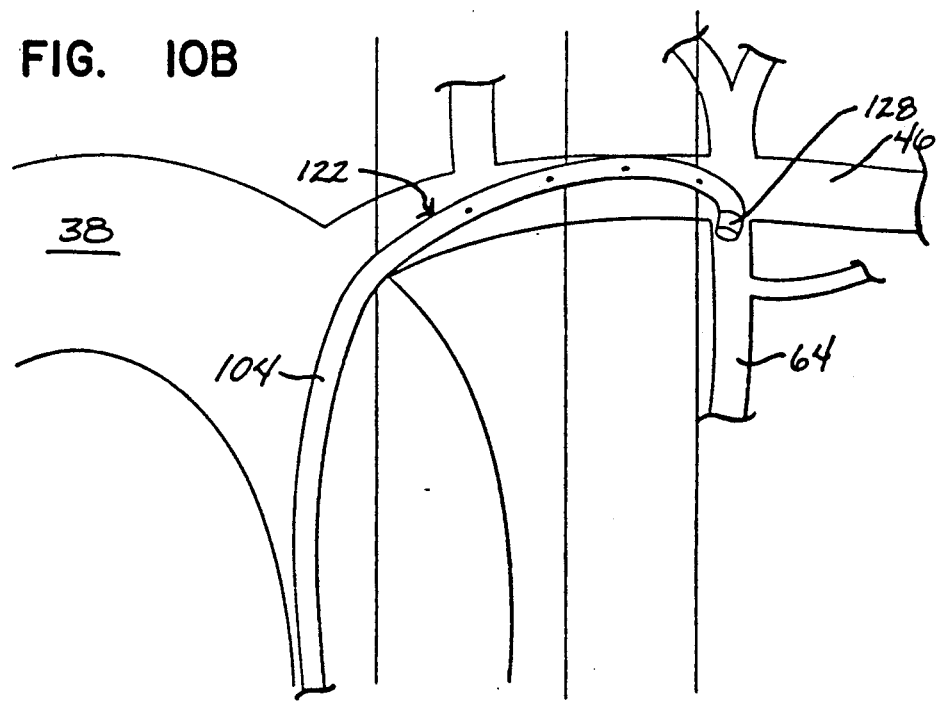
FIG. 10B is a cross sectional diagram of the left subclavian and LITA showing a certain distance of the LITA from the aorta/left subclavian bifurcation, necessitating a series of catheter lengths to accommodate varying distances.

Curve A properly positions catheter 104 in left subclavian 46 at its origin 78 from aorta 16. Referring to FIGS. 7B and 10, the length of the shaft comprising curve "C" is 2, 3, 4, or 5 centimeters, etc., according to the distance of LITA 64 from the left or right innominate aortic bifurcation.

Accordingly, distal catheter tip 138 preferably comprises a pliable atraumatic tip 128 molded securely to distal catheter tip 138. Catheter proximal hub 108, its lumen 112, side ports 118, and end port(s) 114 may be formed by conventional techniques standard in the catheter industry. Distal atraumatic soft tip 128 is readily produced by conventional techniques of standard material in the soft tip catheter industry, although with certain structural features of hingability and method use as incorporated in a novel manner according to the present invention. Bonding of proximal hub 108 and distal soft tip 128 to catheter 104 are also techniques standard in the catheter industry. A conventional radiopaque material is commonly blended into the shaft and tip to allow exact X-ray fluoroscopic location and orientation of the catheter and its soft tip.

A method and apparatus is disclosed for placing a catheter with a canted, deformable, atraumatic tip, end port, and a curved firm shaft with side ports, into the origin of a normal or displaced left subclavian artery and advancing it over a guidewire into the origin of the left internal thoracic artery through a femoral artery puncture site. The soft, gentle, canted, deformable, short tip of the catheter permits atraumatic injection of radiopaque contrast material into the entire left internal thoracic artery and all of its branches. In the subclavian 46 the curved shaft with side ports, just proximal to the left internal thoracic artery, permits nontraumatic firm catheter tip support while contrast exits the side ports of the catheter allowing simultaneous visualization of the left subclavian and left internal thoracic artery.

Figure 11D:
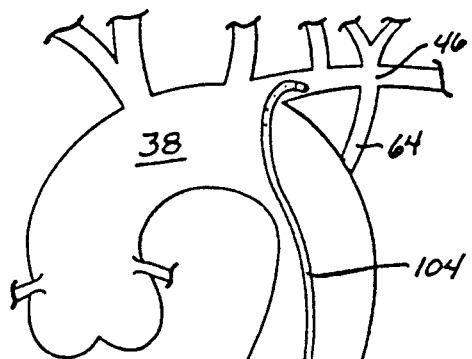
FIGS. 11 (A-L) are cross sectional diagrams of the aortic arch, descending thoracic, abdominal and iliac vessels, and the left subclavian LITA combinations demonstrating serially the method of insertion of the invented catheter.
Figure 11E:
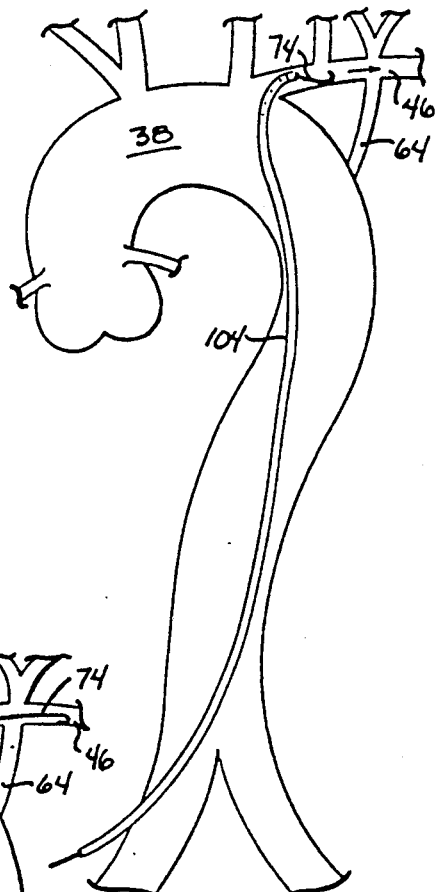
Figure 11F:
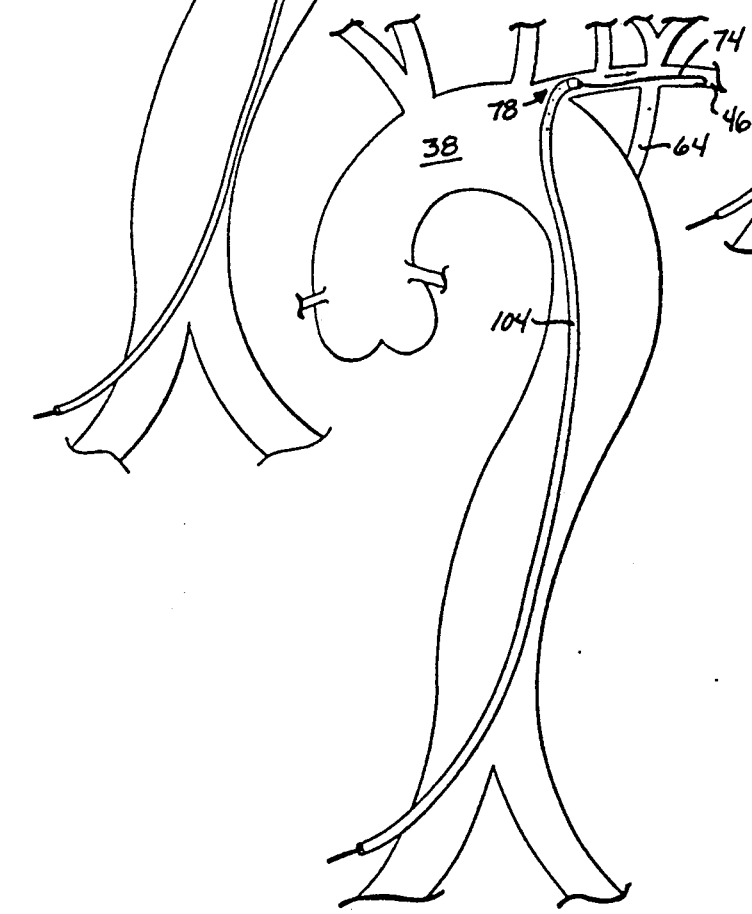

Referring now to FIGS. 11A–11E, there is disclosed the techniques for cannulating the LITA and using the apparatus of the present invention. The process involves percutaneous insertion of a "J" tipped guidewire into the femoral artery, and then advancing it under fluoroscopic control past left subclavian artery origin 78 into a proximal portion of aortic arch 38. Holding the proximal end of the wire, catheter 104 is threaded over guidewire 74 into the proximal portion of aortic arch 38 beyond the left subclavian origin 78. Thereafter the wire is withdrawn into the catheter shaft in a manner sufficient to prevent deformation of the catheter curves. Catheter 104 is slowly rotated and withdrawn until soft deformable atraumatic tip 128 hooks the normal or displaced left subclavian artery origin. Guidewire 74 is then again advanced into catheter 104 until it deforms and straightens out distal soft tip 128. The flexibility and hinge-like characteristics of the curves B and D, joining the soft, pliable tip 128 to distal catheter tip 138, 138' permits curves B and D to straighten, thus offering the least resistance to wire advancement, into left subclavian artery 46. This also minimizes any recoil of the catheter tip out of the displaced left subclavian artery. The guidewire is then positioned past the origin of the LITA, as illustrated in FIG. 11F.

Guidewire 74 is then withdrawn into catheter 104 apparatus so that it is not deforming any of the curves. Catheter 104 is then rotated and withdrawn slowly. If the catheter does not enter the LITA, it is presumed that the LITA is arising from the left thyrocervical trunk 86. In such instance, guidewire 74 is repositioned past the LITA origin 142 into the distal left subclavian artery, and catheter 104 apparatus is again advanced over guidewire 74 into this position. Guidewire 74 is then withdrawn into the apparatus such that it is proximal to all the catheter curves. The catheter is then again slowly rotated (preferably in the opposite direction from previously) and withdrawn until it enters the left thyrocervical trunk 86. Slight advancement of catheter 104, thereafter, permits entry into the superiorly-anteriorly located LITA arising from the left thyrocervical trunk.

Figure 12:
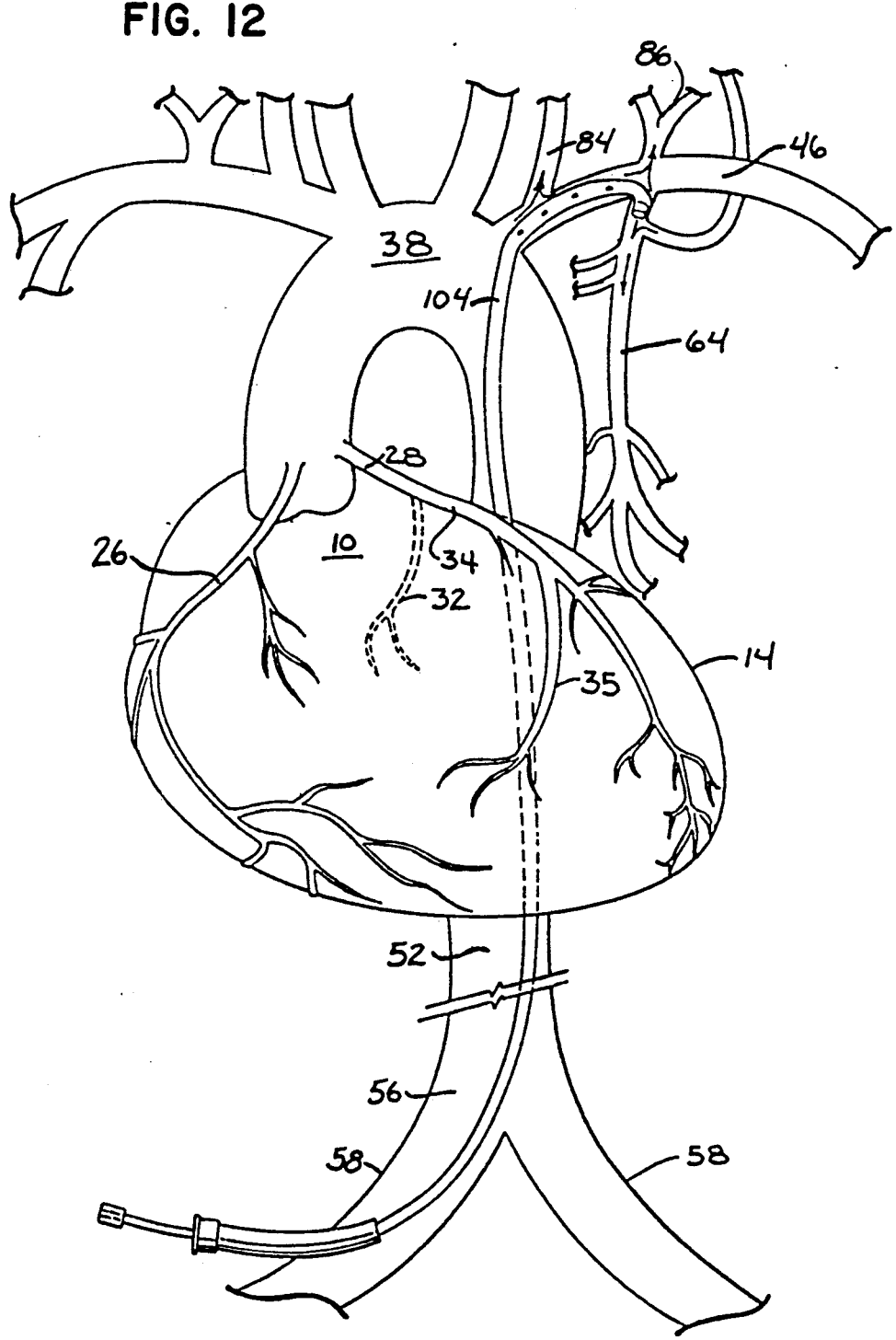
FIG. 12 is a cross sectional diagram of the heart, aortic and iliac areas, left subclavian and LITA. The invented apparatus is seen positioned in the LITA with simultaneous visualization of the left subclavian and its branches, left thyrocervical trunk and its branches, the LITA and its proximal transverse branch, and all other branches of the LITA.

With the apparatus of the invention positioned as illustrated in FIG. 12, angiographic radiopaque contrast is injected into proximal end port 106. This material flows through catheter lumen 112 and exits first through side ports into the left subclavian 46 and finally through the end port 114 surrounded by soft deformable tip 128. This permits complete visualization of the entire left subclavian-LITA and the branches simultaneously.

Figure 13:
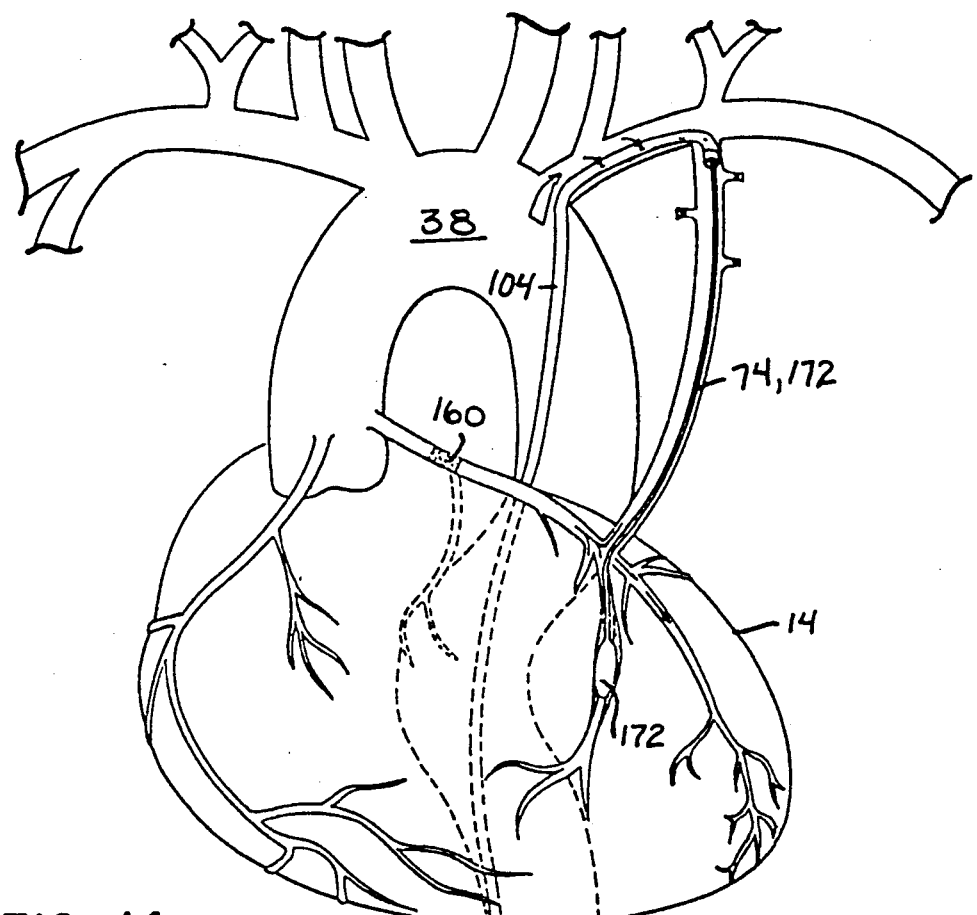
FIG. 13 is a cross sectional diagram of the aorta, left subclavian and LITA bypass graft anastomosed to the left anterior descending coronary artery. A PTCA balloon wire apparatus is inserted through the invented apparatus into a blockage in the left anterior descending coronary artery beyond the LITA-LAD anastomosis. The diagram emphasizes the importance of continuous blood flow through the subclavian side holes of the invented apparatus, and said blood flowing along the lumen of the invented apparatus and into the distal end port, surrounded by the soft tip, then exiting into the LITA. Blood flow continues down the LITA to all areas of the bypassed vessel permitting continuous blood supply to the heart muscle during the angioplasty procedure.
Figure 14:
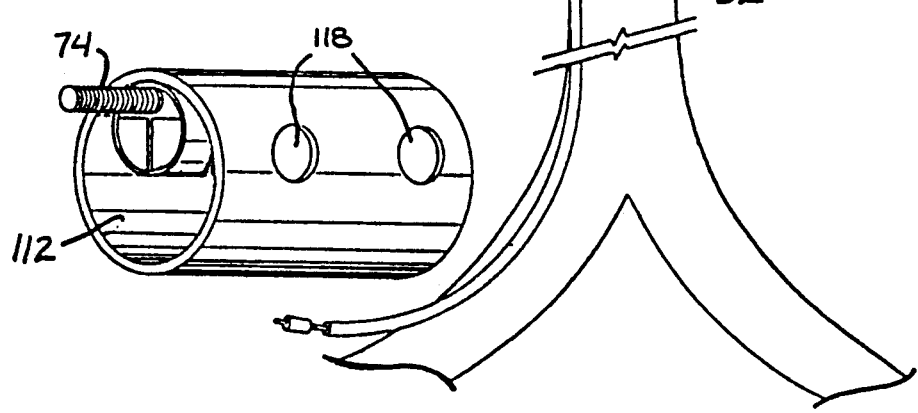
FIG. 14 is a cross section of the invented apparatus with a PTCA wire inserted into the shaft of a PTCA balloon catheter demonstrating the residual lumen in the invented apparatus permitting blood flow through the side ports and through the remaining lumen in the invented apparatus.

Embodied in FIG. 13, the catheter 104 of the present invention is shown inserted through a percutaneous insertion in the right common femoral artery 58 and following the accordionized iliac artery 56, the abdominal aorta 52 and thoracic aorta 54, and into the geriatrically displaced left subclavian artery 46. The device is shown selectively inserted into an anterior-inferior located LITA 64. The LAD 34 is totally occluded at 160 and the LITA 64 has been surgically anastomosed at 164 distal to original total occlusion 160. A new, or unrecognized, pre-operative stenosis at 168 beyond LITA-LAD anastomosis 164 is visualized by injection of contrast. A guidewire 74 is then advanced through the catheter shaft into LITA 64 and LAD 34, and across new stenosis 168. An apparatus to remove arterial stenosis (such as a PTCA balloon 172, atherectomy device, impregnable chemical, or the like), is advanced over the wire, through the LITA, and into the new stenosis. The tip 128 of catheter 104 of the present invention will completely occlude blood flow around the catheter into the LITA. Thus, the plurality of side ports 118 provides continuous blood profusion of the coronary circulation by blood entering the side ports in subclavian artery 46 and exiting the end port 106 into LITA 64. FIG. 14 demonstrates an exemplary relative cross-sectional area available for blood to enter side ports 118 and flow through the invented guiding catheter 104 lumen 112 even with a PTCA balloon 172 and PTCA wire 74 in place.

Figure 15:
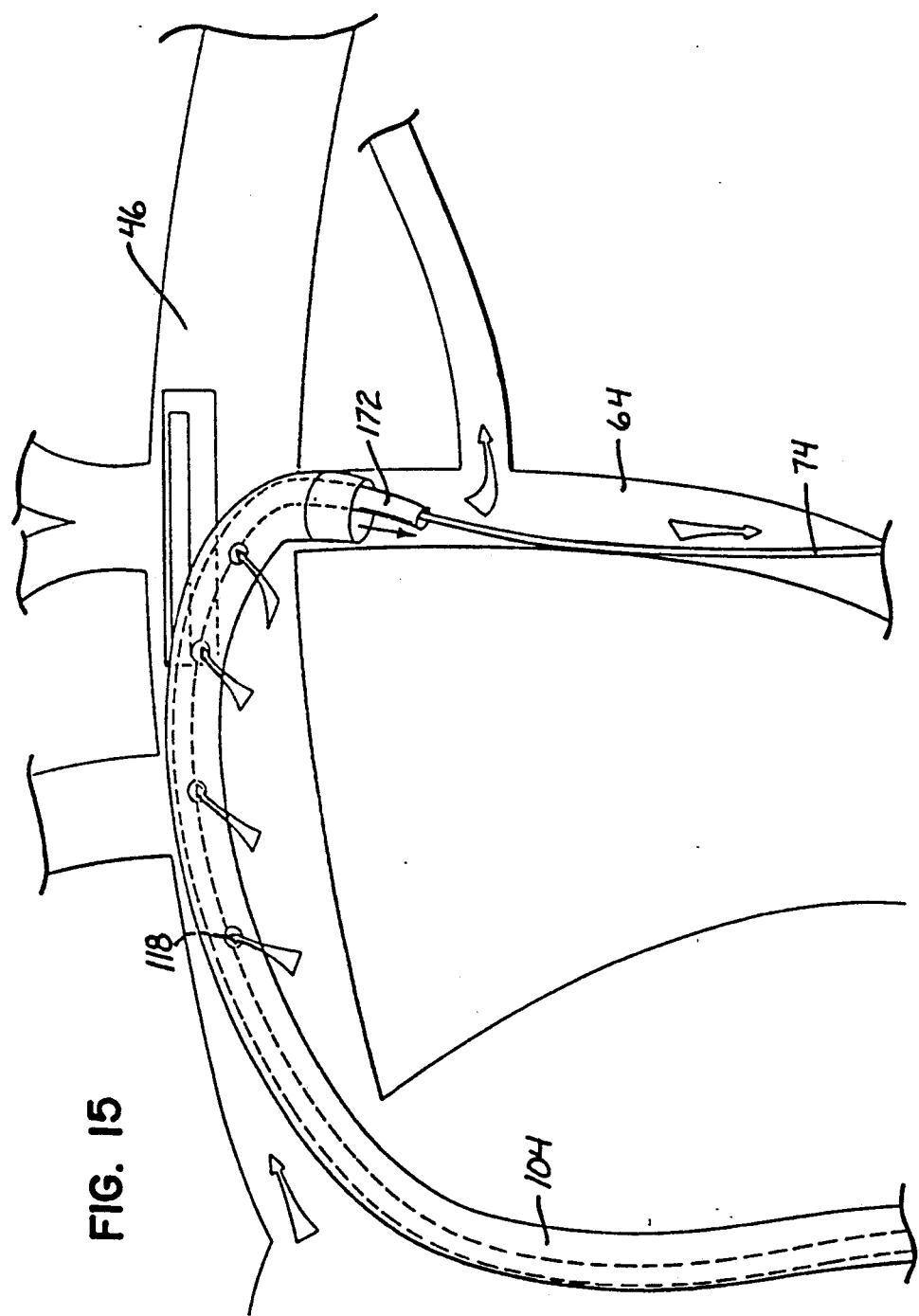
FIG. 15 is a cross sectional diagram of the aortic arch and left subclavian with the invented apparatus positioned in the LITA demonstrating blood flow through the side holes via the left subclavian with exit into the LITA with the balloon wire apparatus in place in the LITA.

In FIG. 15, the guiding catheter 104 of the present invention has an exemplary internal available lumen of 0.065–0.080 inches depending on the French size chosen. The external diameter of a usual balloon catheter shaft ranges from 0.022 inches (1.7 French) to 0.060 inches (4.5 French) with the average shaft being 0.039 inches (3 French). Even with the smallest diameter guide, this will leave 0.026 inches for blood to enter a side port 118 around balloon catheter 104 shaft and travel along the lumen of the invented apparatus to exit through end port 118 in the LITA 64.

Figure 16:
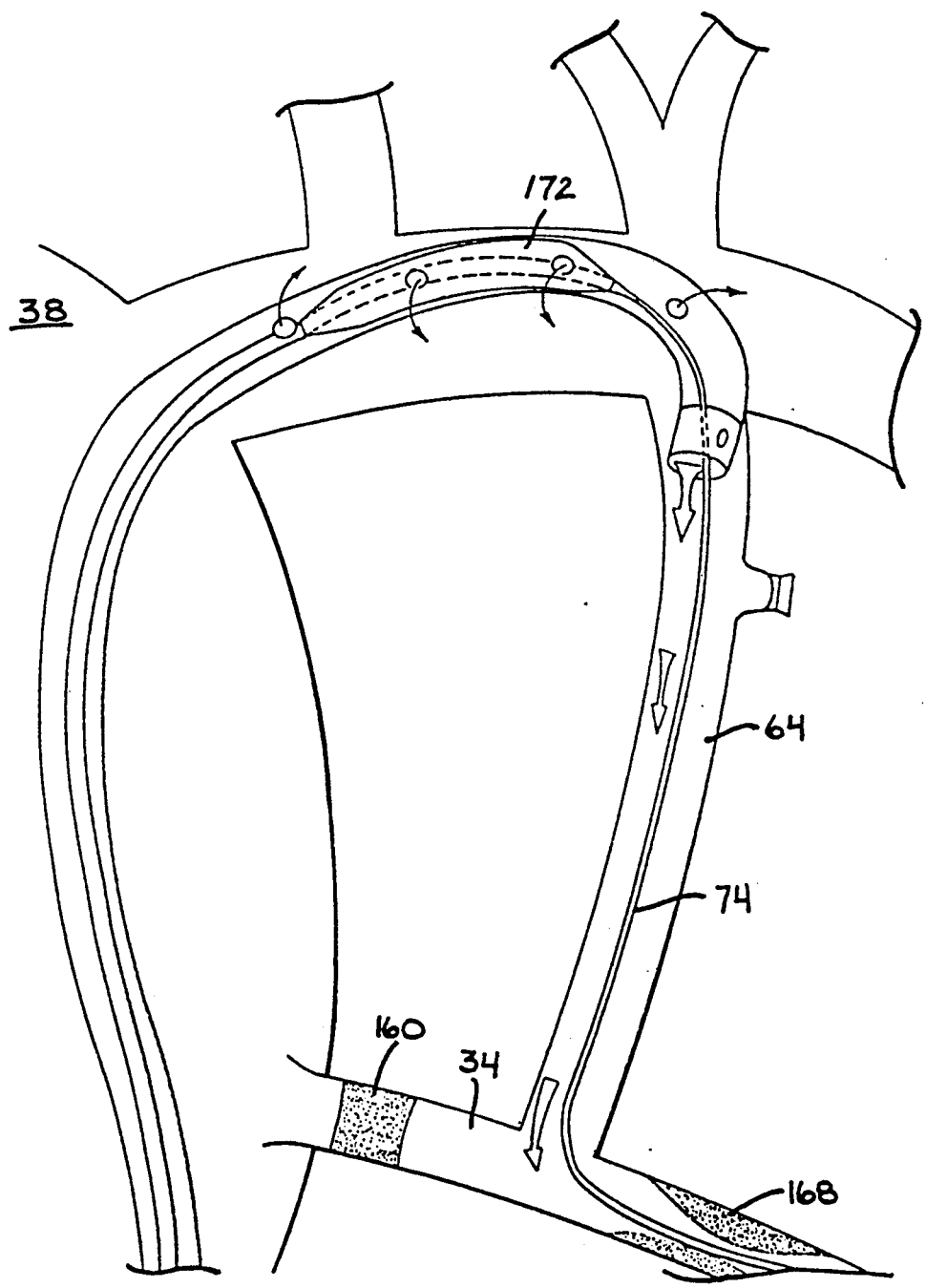
FIG. 16 is a cross sectional diagram of the aorta, left subclavian, LITA bypass graft and left anterior descending coronary artery after there has been successful partial resolution of a blockage in the left anterior descending coronary artery. The PTCA wire remains across the treated partially resolved stenosis while the balloon has been withdrawn into the curve "C" of the invented apparatus in order that the partially deflated unwrapped balloon may occlude most of the side holes in the invented apparatus shaft in order to inhibit contrast exit through these side ports and favor contrast exit into the LITA in order to visualize the area of recent PTCA.
Figure 17:
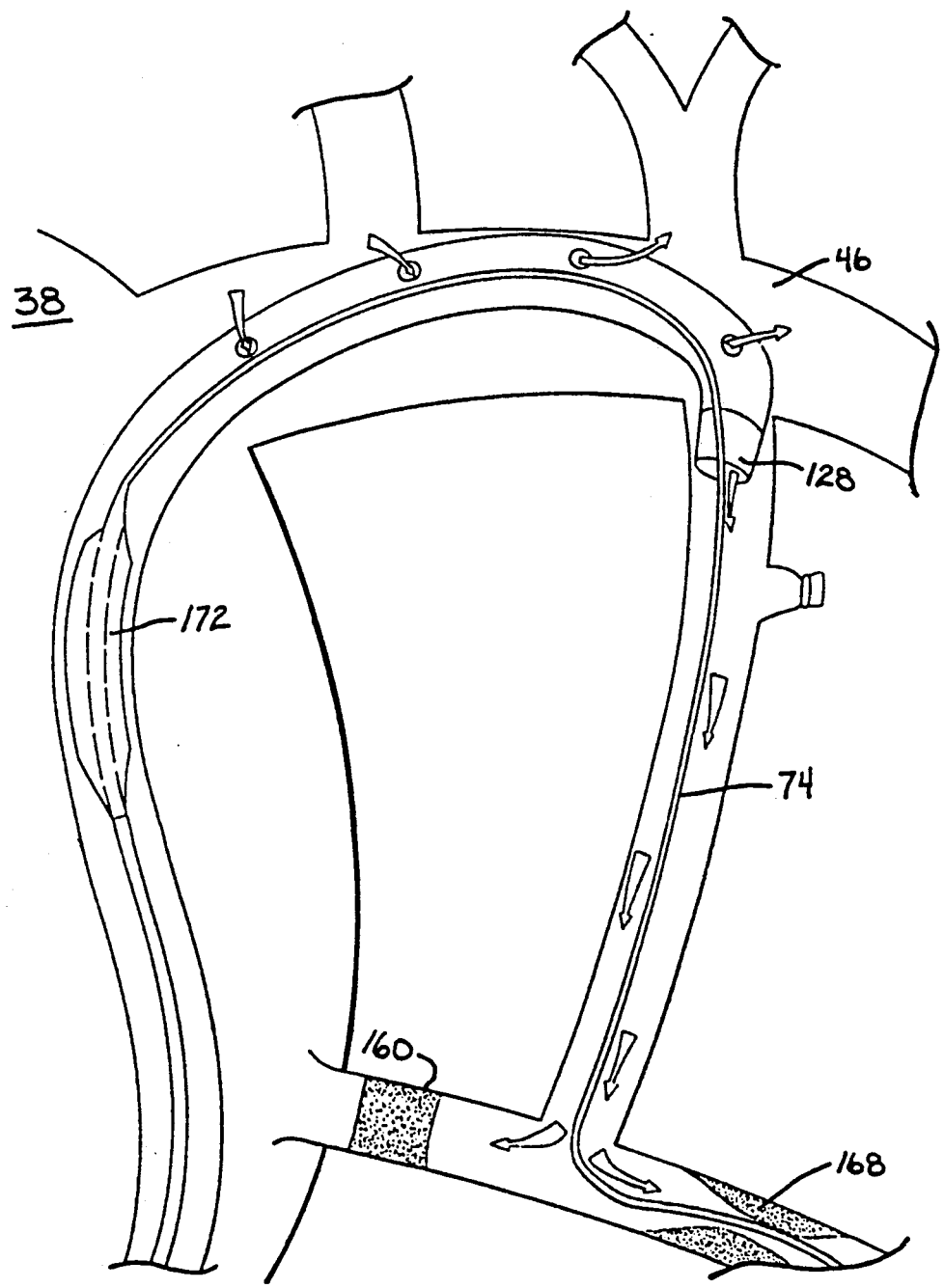
FIG. 17 is a cross sectional diagram of the aorta, left subclavian, LITA bypassed graft anastomosed to the left anterior descending coronary artery and the partially resolved blockage in the left anterior descending coronary artery beyond the LITA-LAD anastomosis. While the PTCA wire remains in the catheter shaft through the LITA and across the partially resolved stenosis the partially deflated unwrapped ballon has been withdrawn from curve "C" into the catheter shaft remaining in the aorta in order that the side holes may become uncovered again and permit blood flow to once again course from the left subclavian through the side ports with exit into the LITA and LAD so that a period of observation can occur to make sure that the recently treated angioplasty site does not rapidly close. Should rapid closure occur, the balloon can be readily advanced over the wire which remains across the partially treated stenosis.
Figure 18:
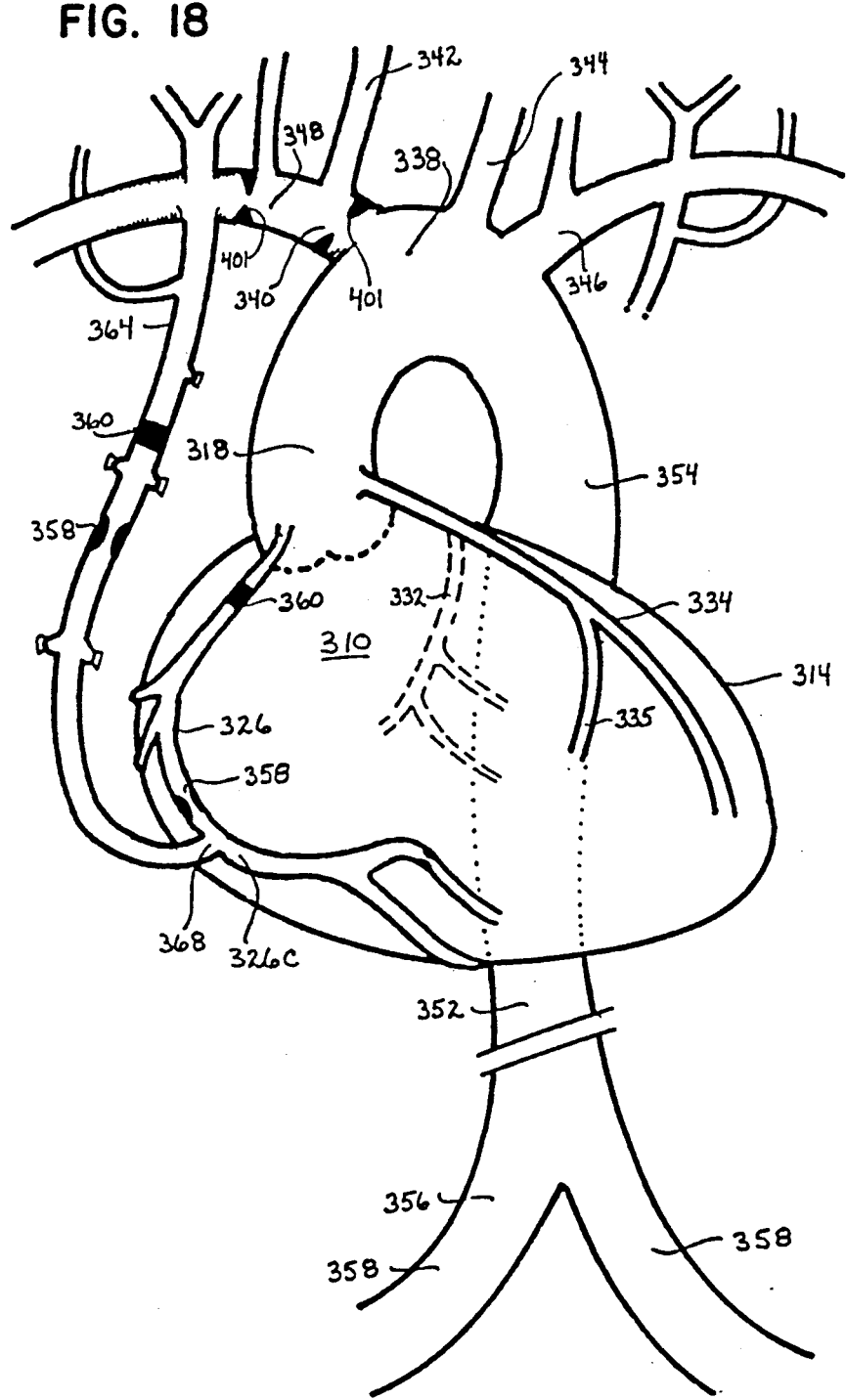
Figure 19A:
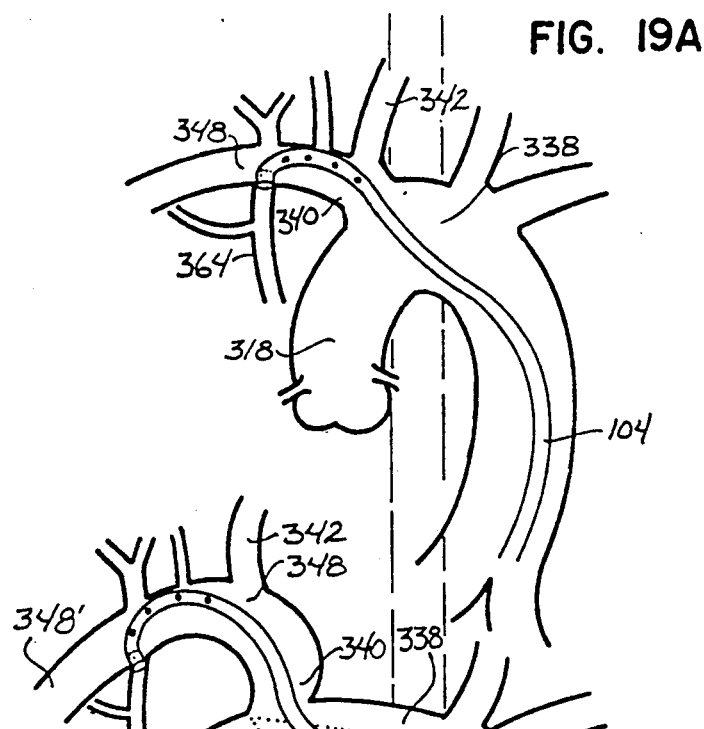
Figure 19B:
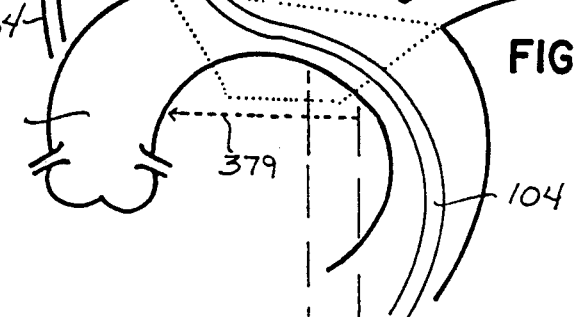
Figure 19C:
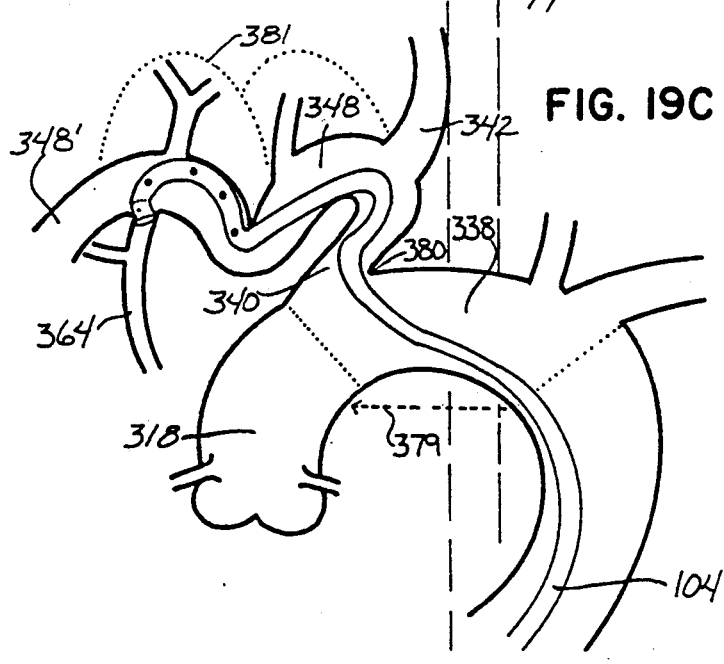
Figure 20A:
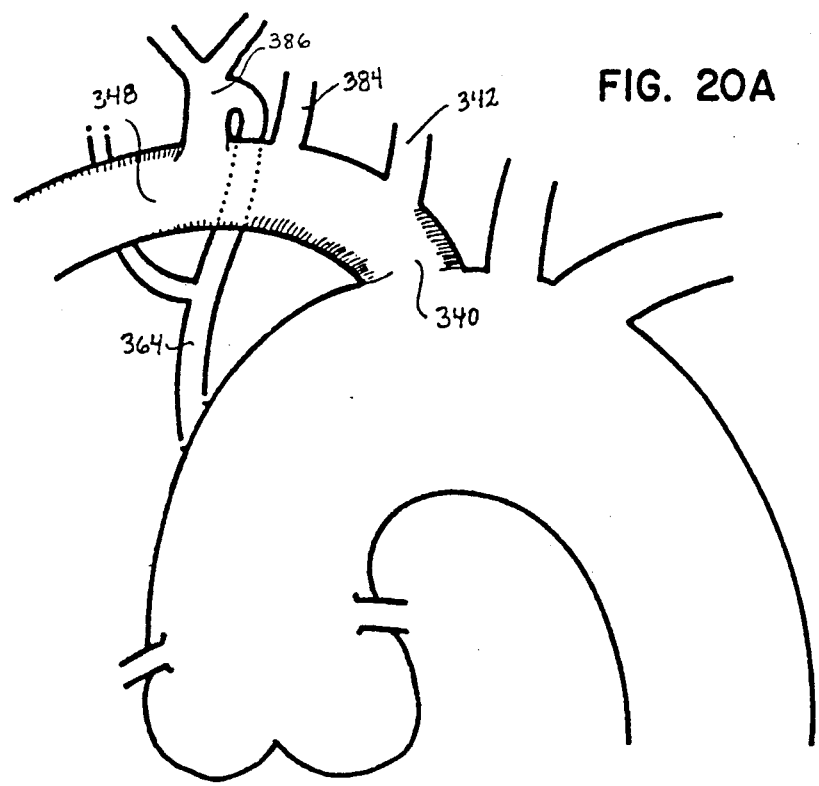
Figure 20B:
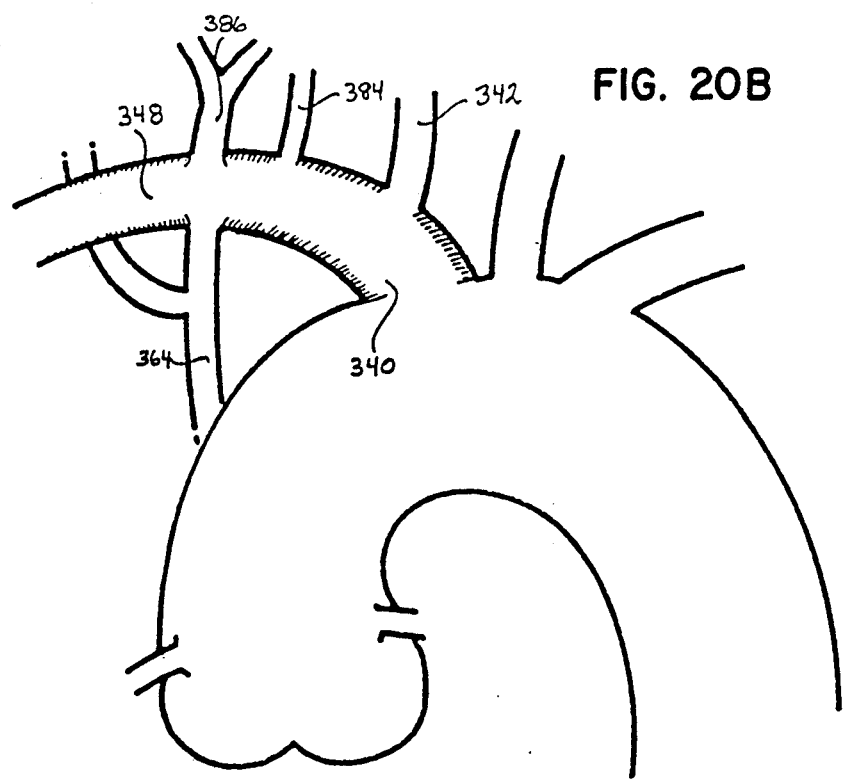
Figure 21A:
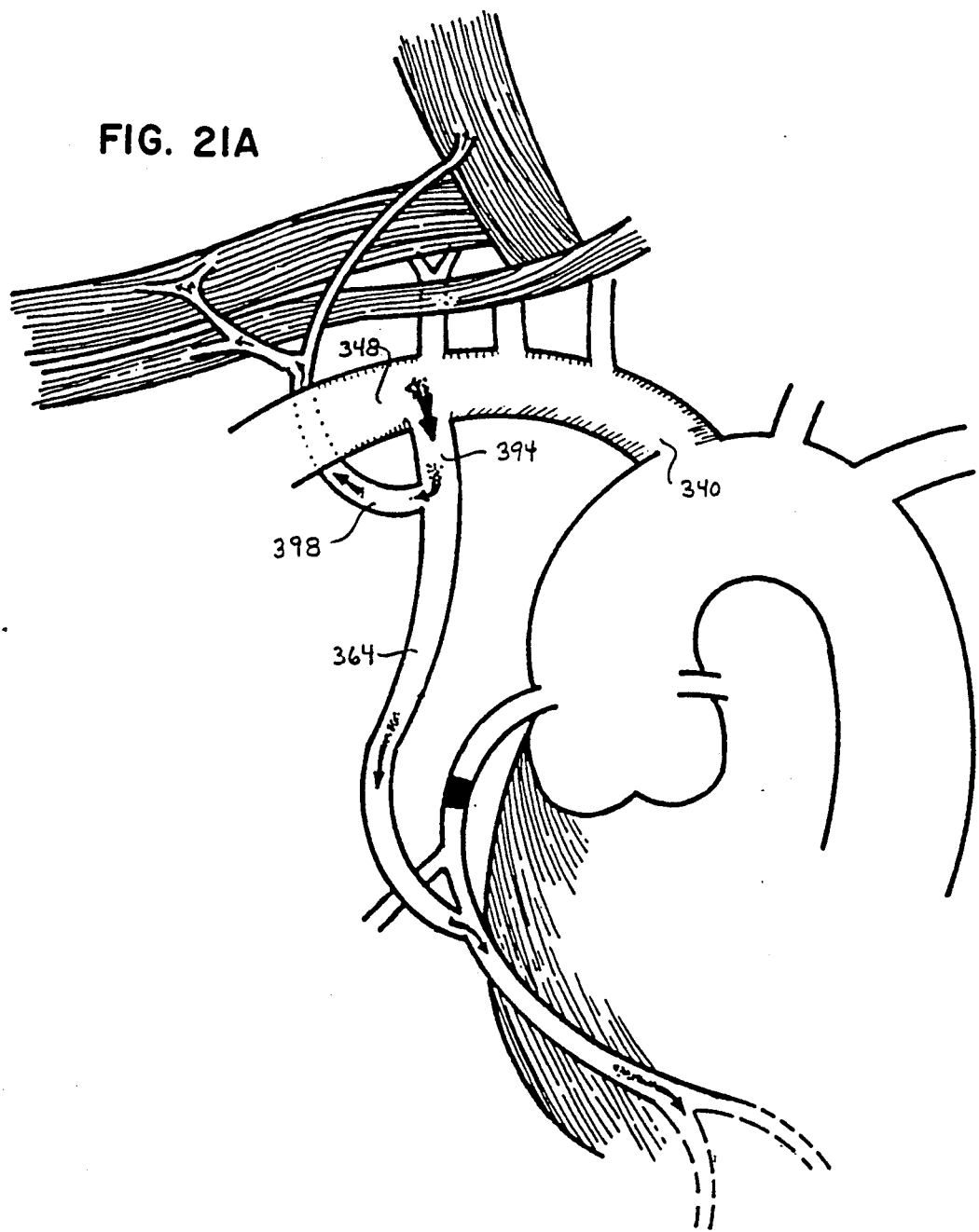
Figure 21B:
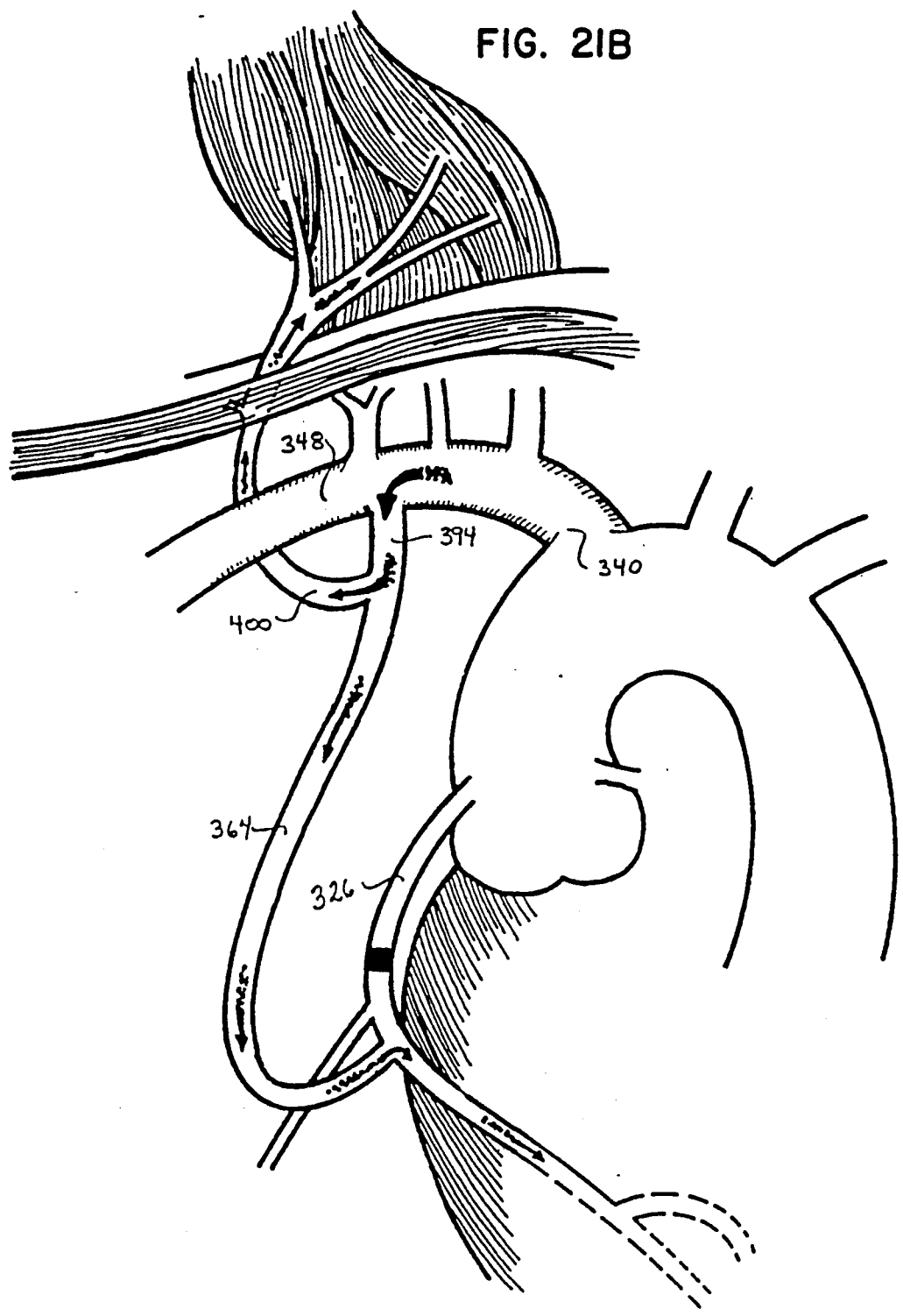
Figure 22:
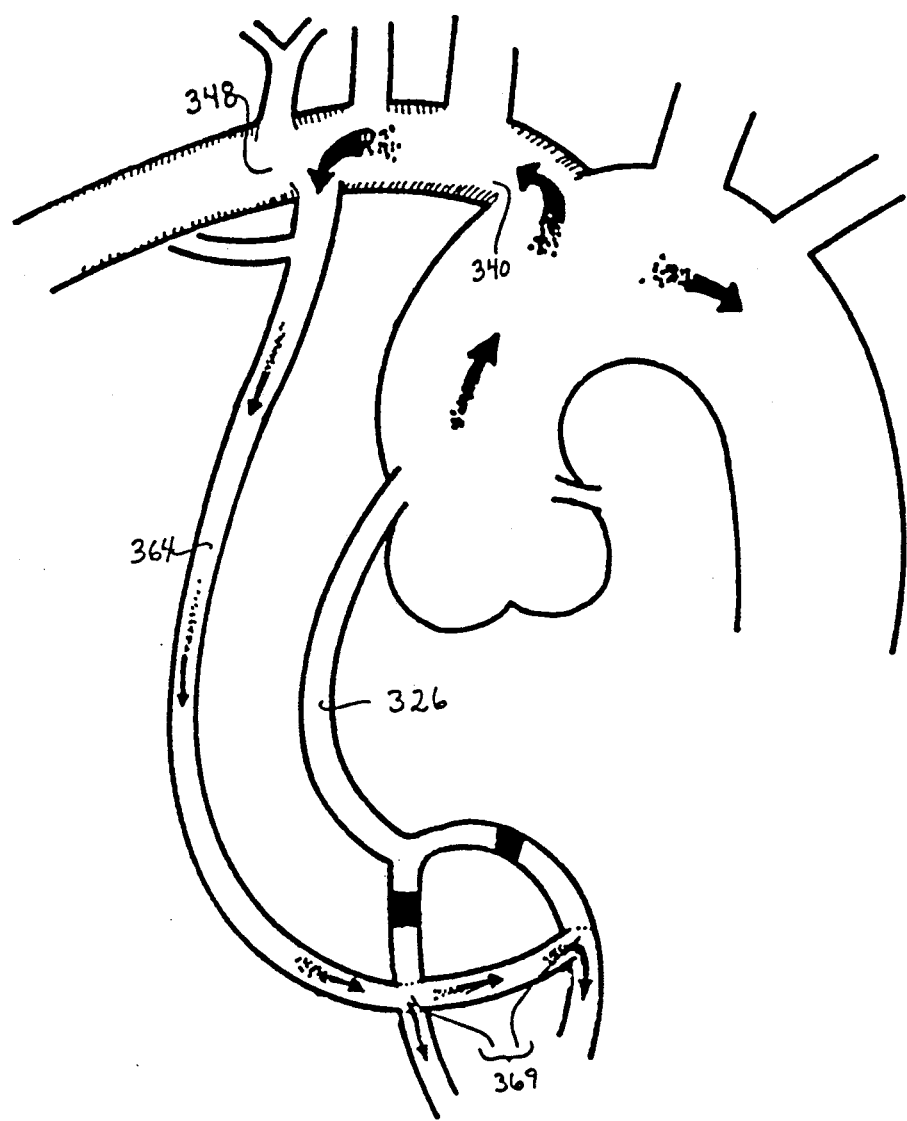
Figure 23:
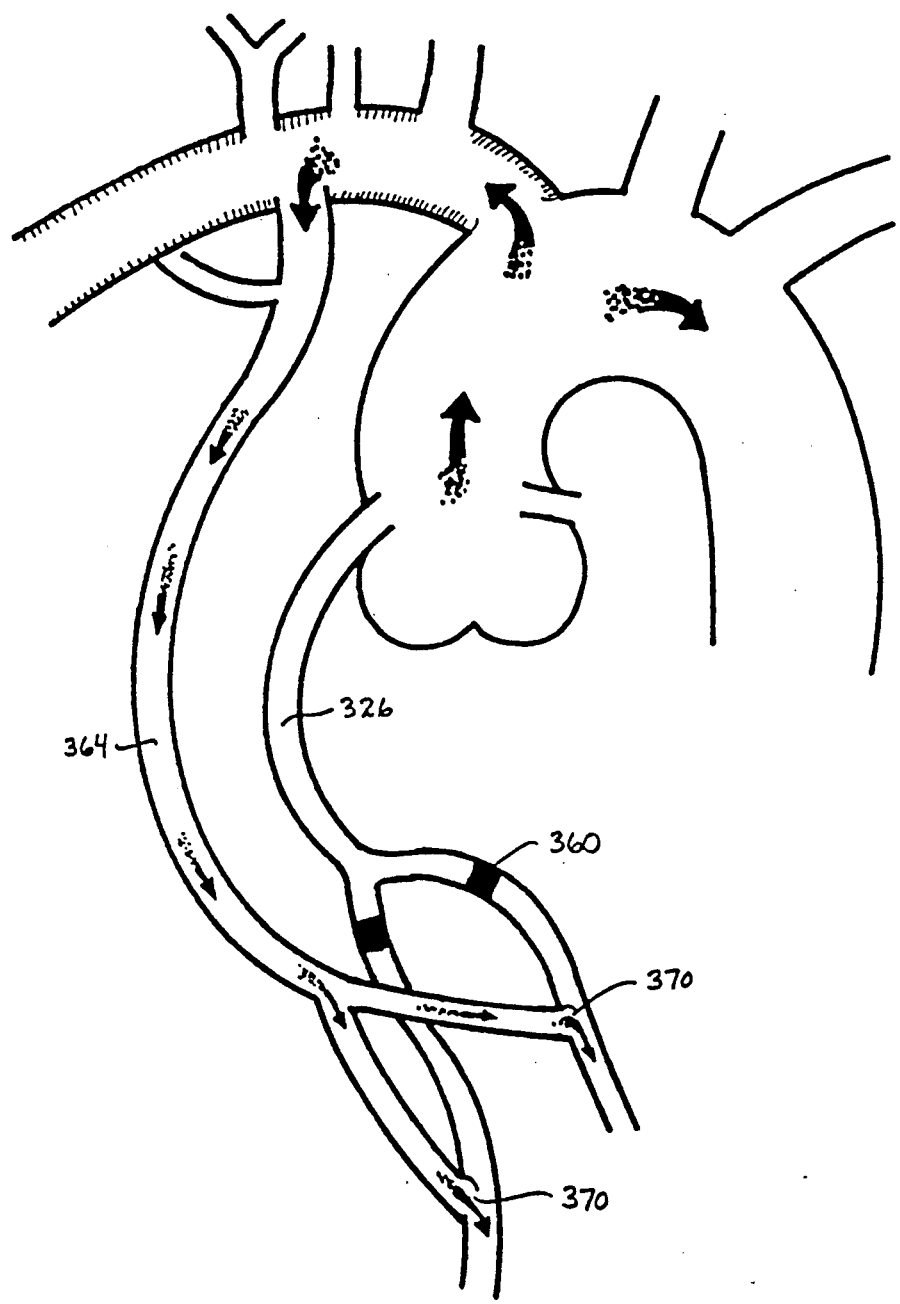
Figure 24A:
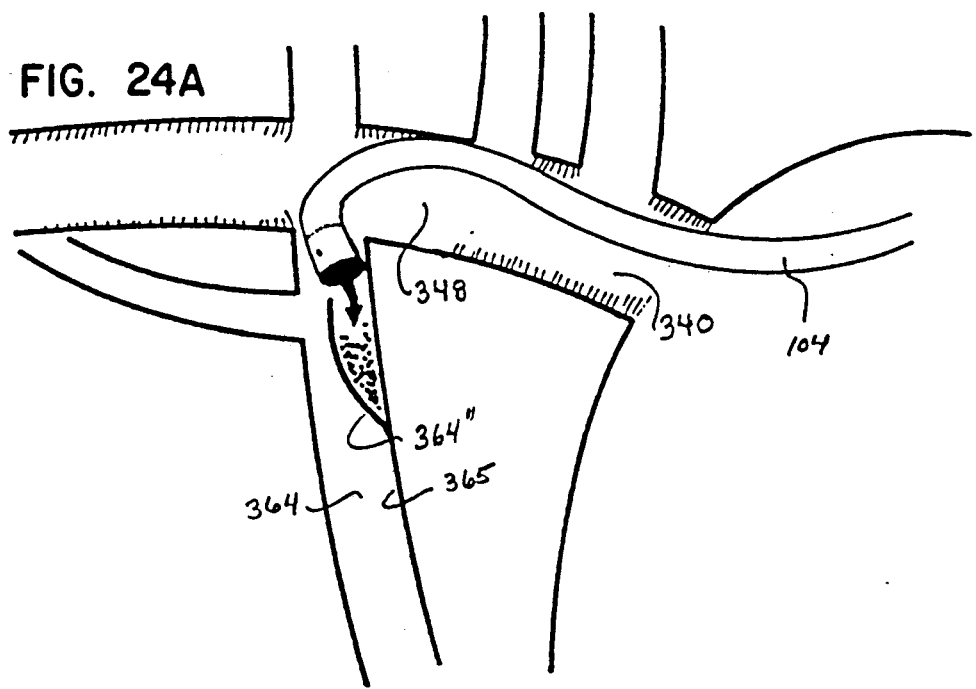
Figure 24B:
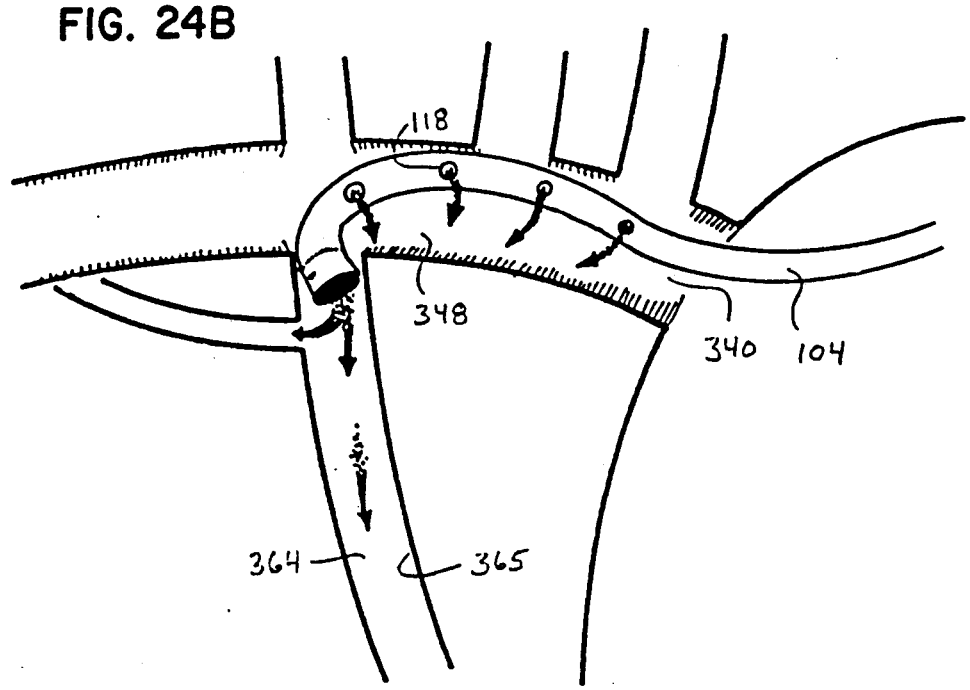
Figure 24C:
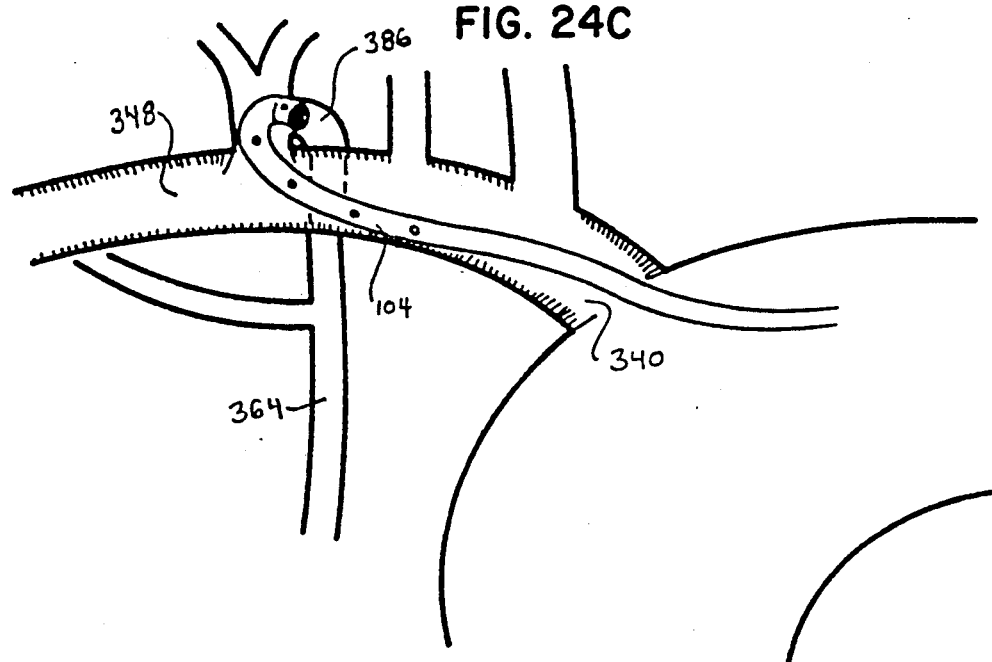
Figure 24D:
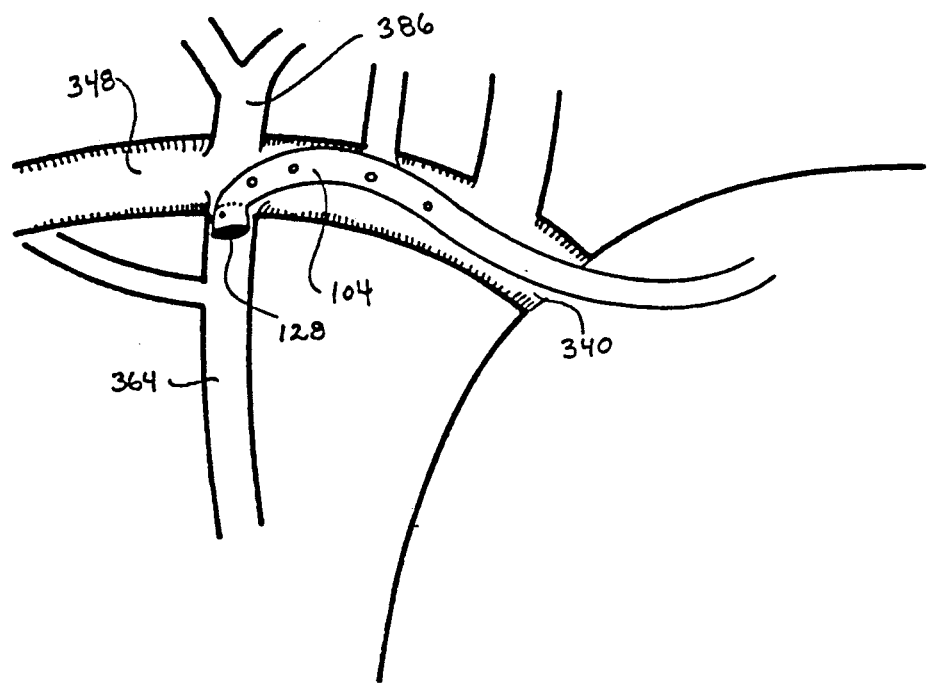
Figure 25:
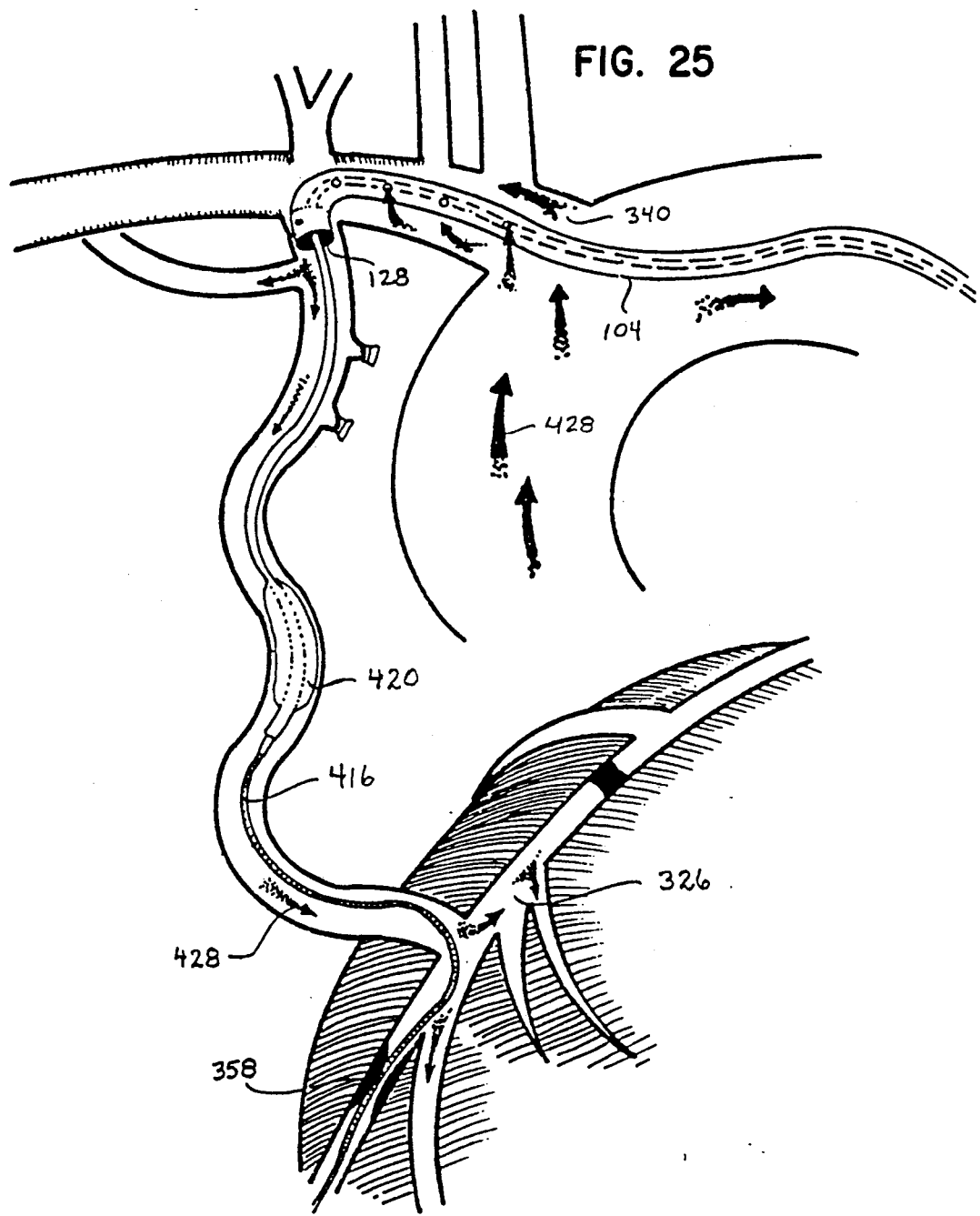
Figure 26A:
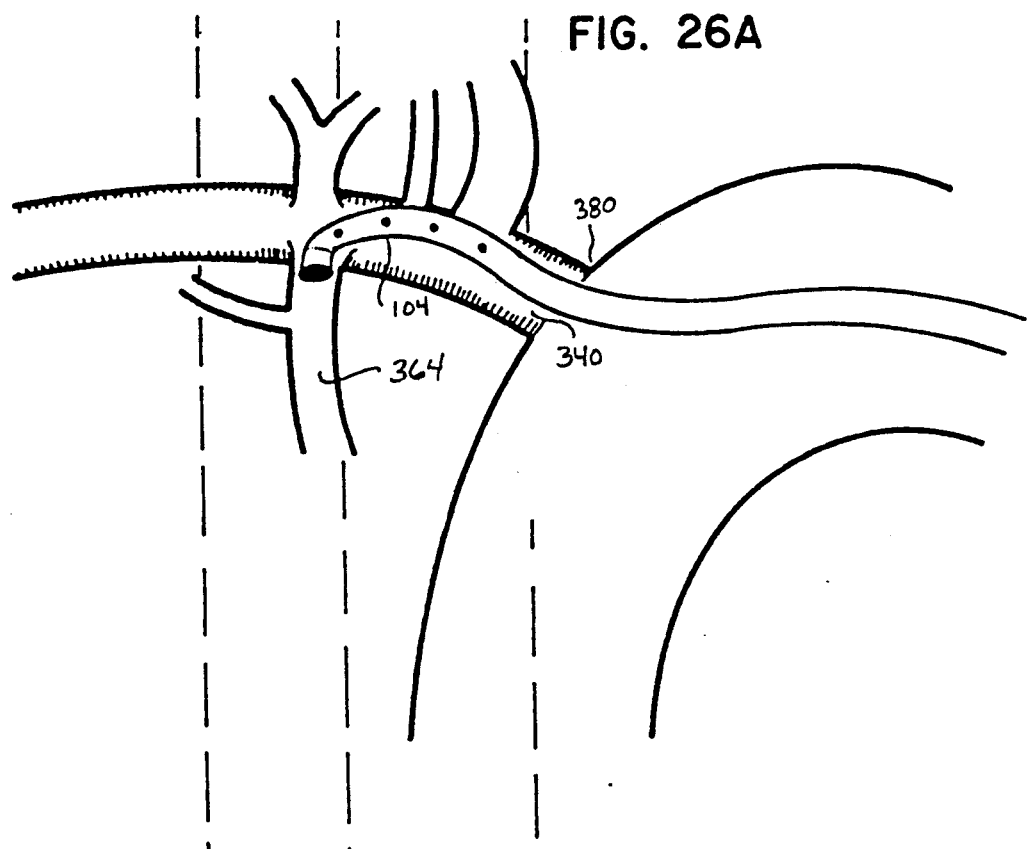
Figure 26B:
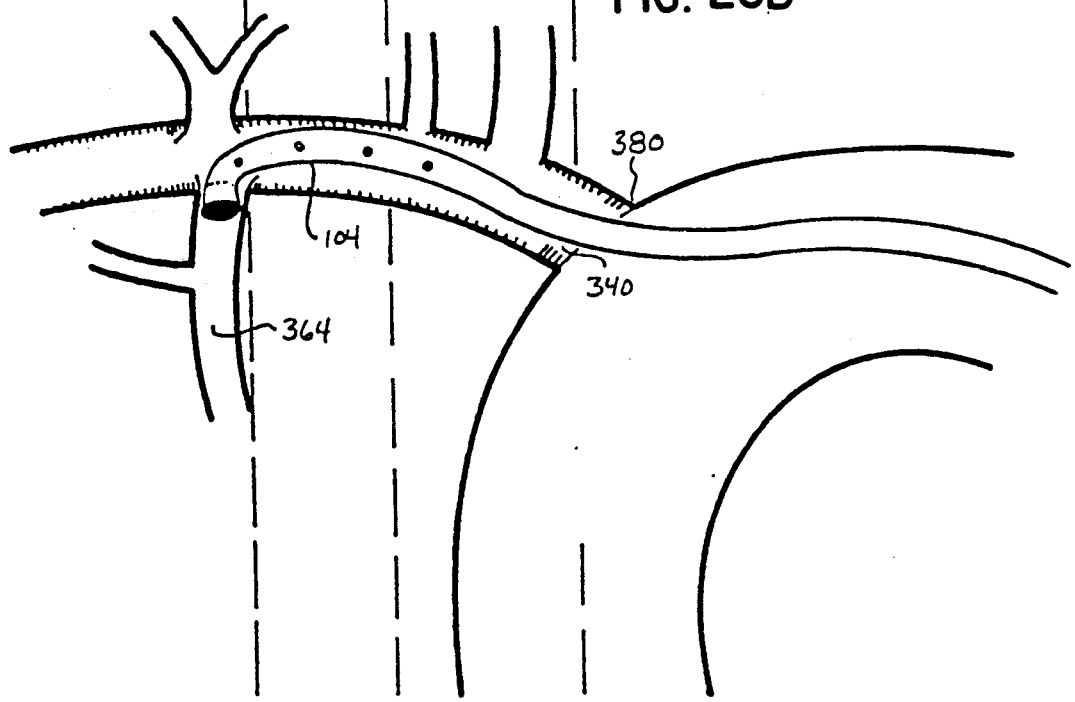
Figure 27A:
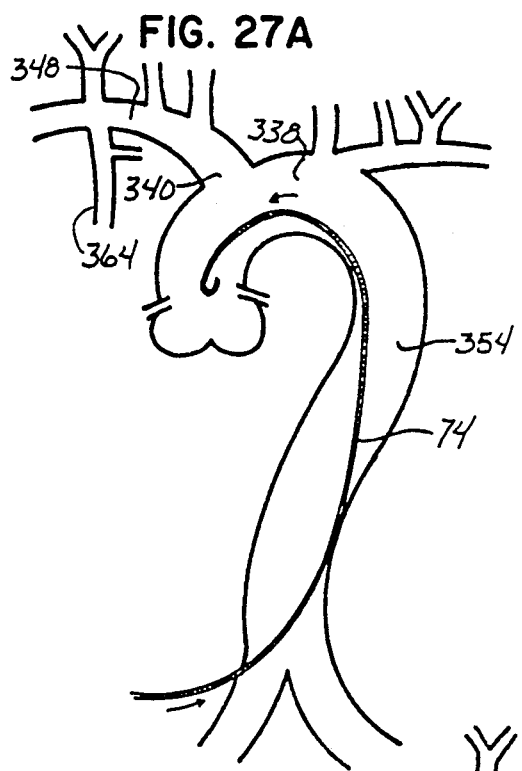
Figure 27B:
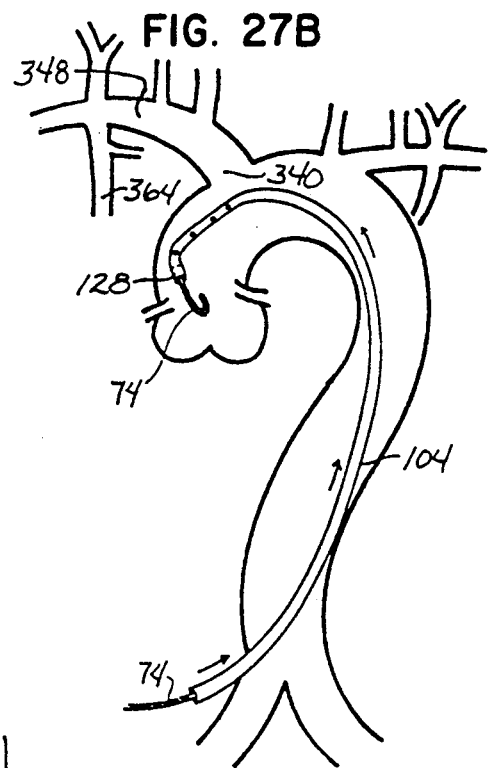
Figure 27C:
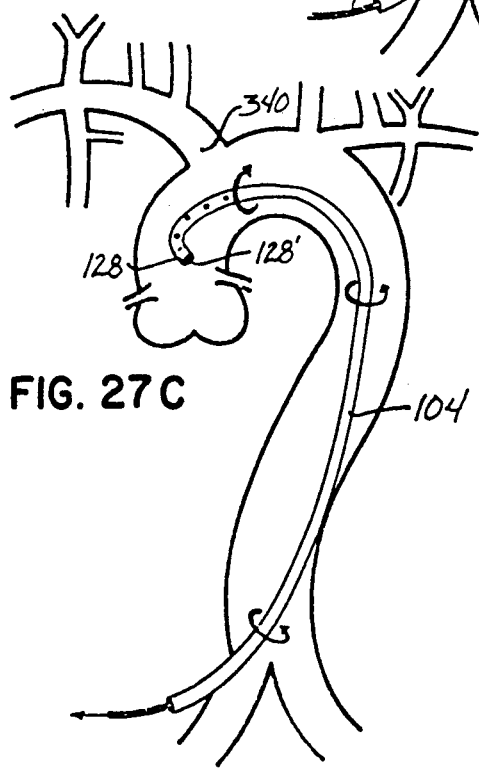
Figure 27D:
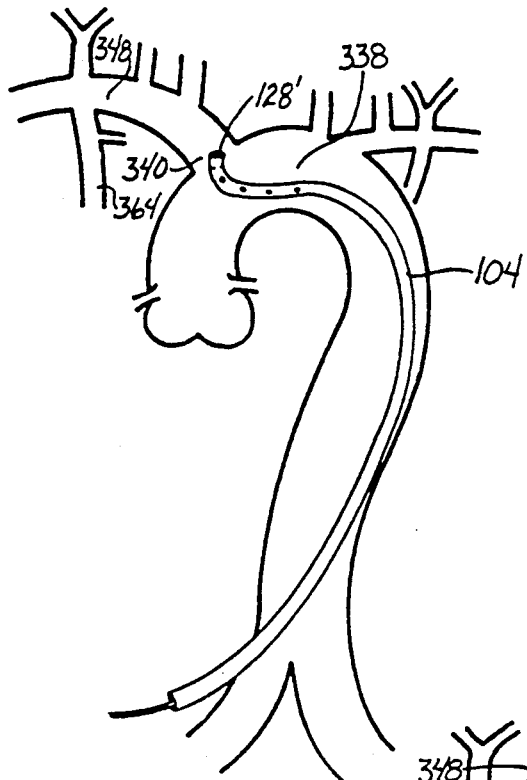
Figure 27E:
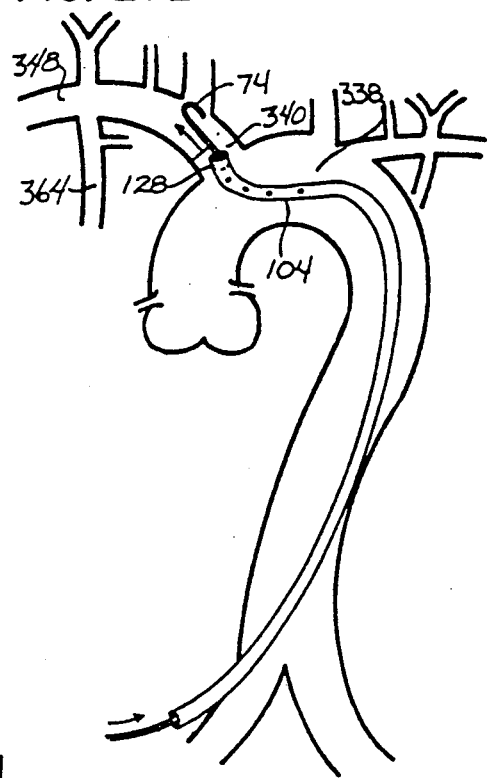
Figure 27F:
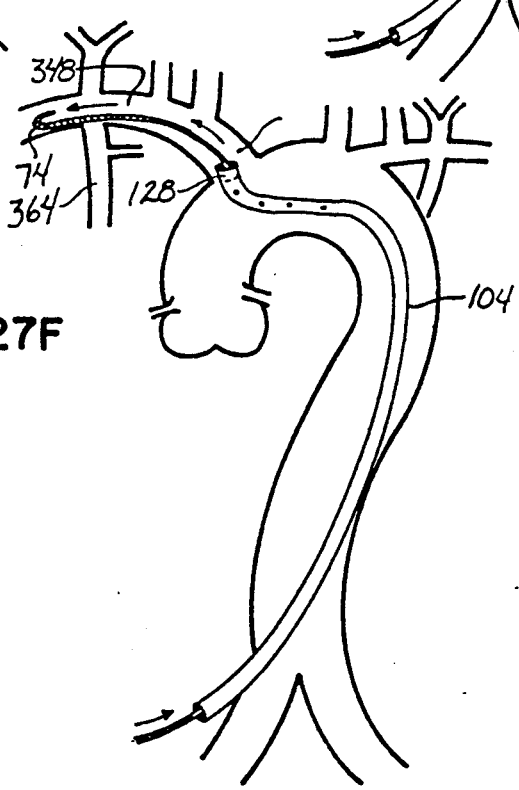
Figure 27G:
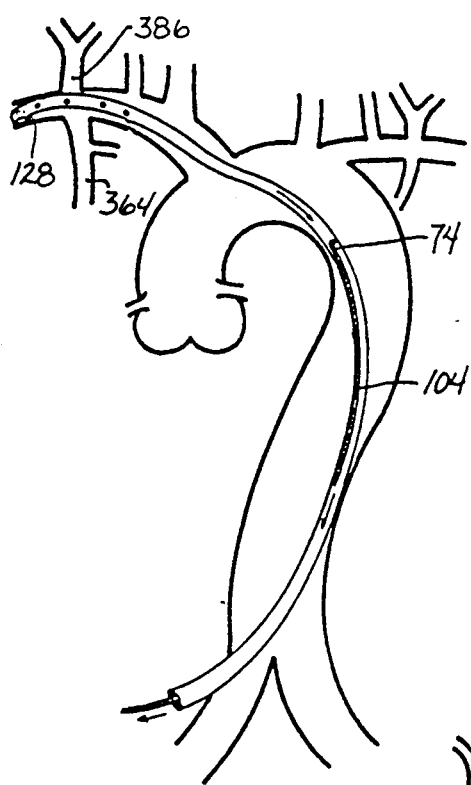
Figure 27H:
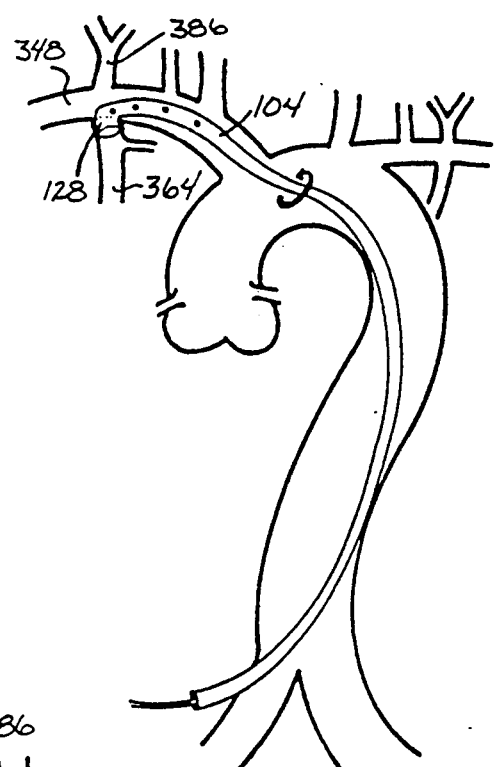
Figure 27I:
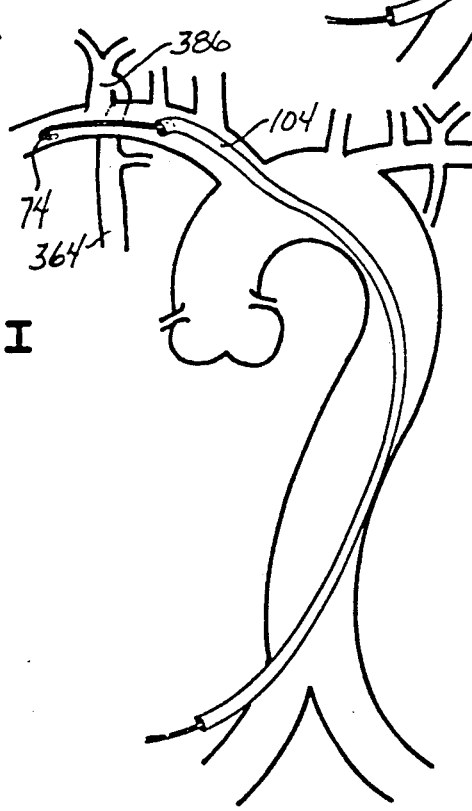
Figure 27J:
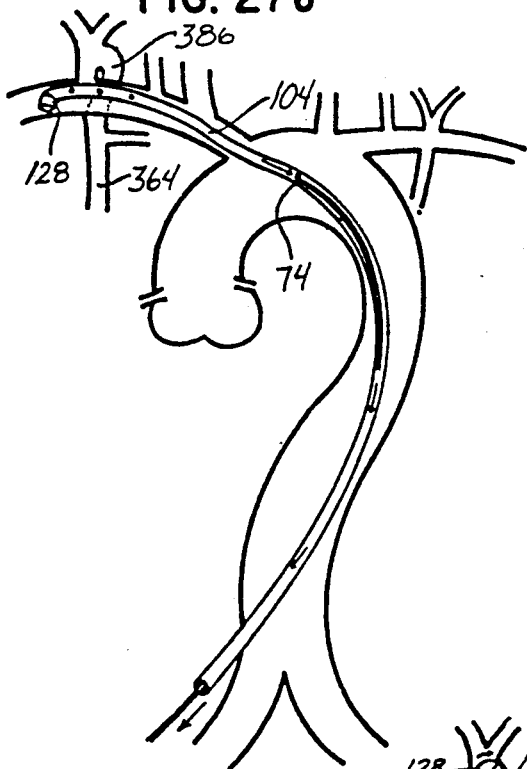
Figure 27K:
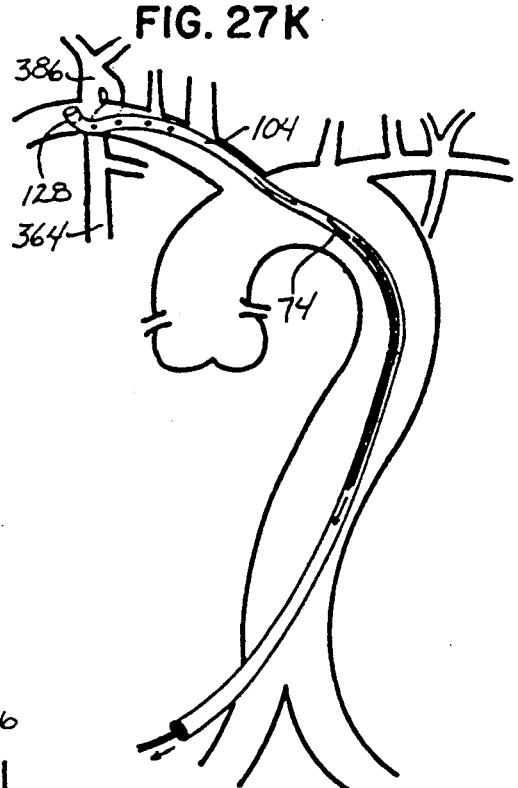
Figure 27L:
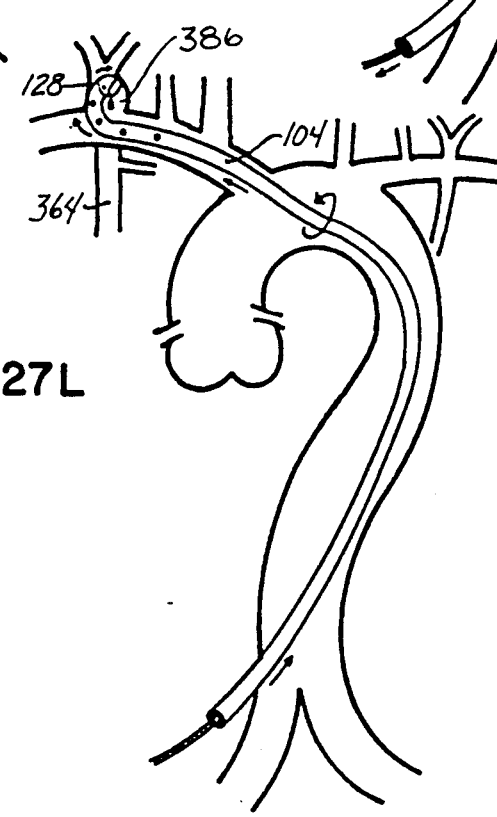
Figure 28:
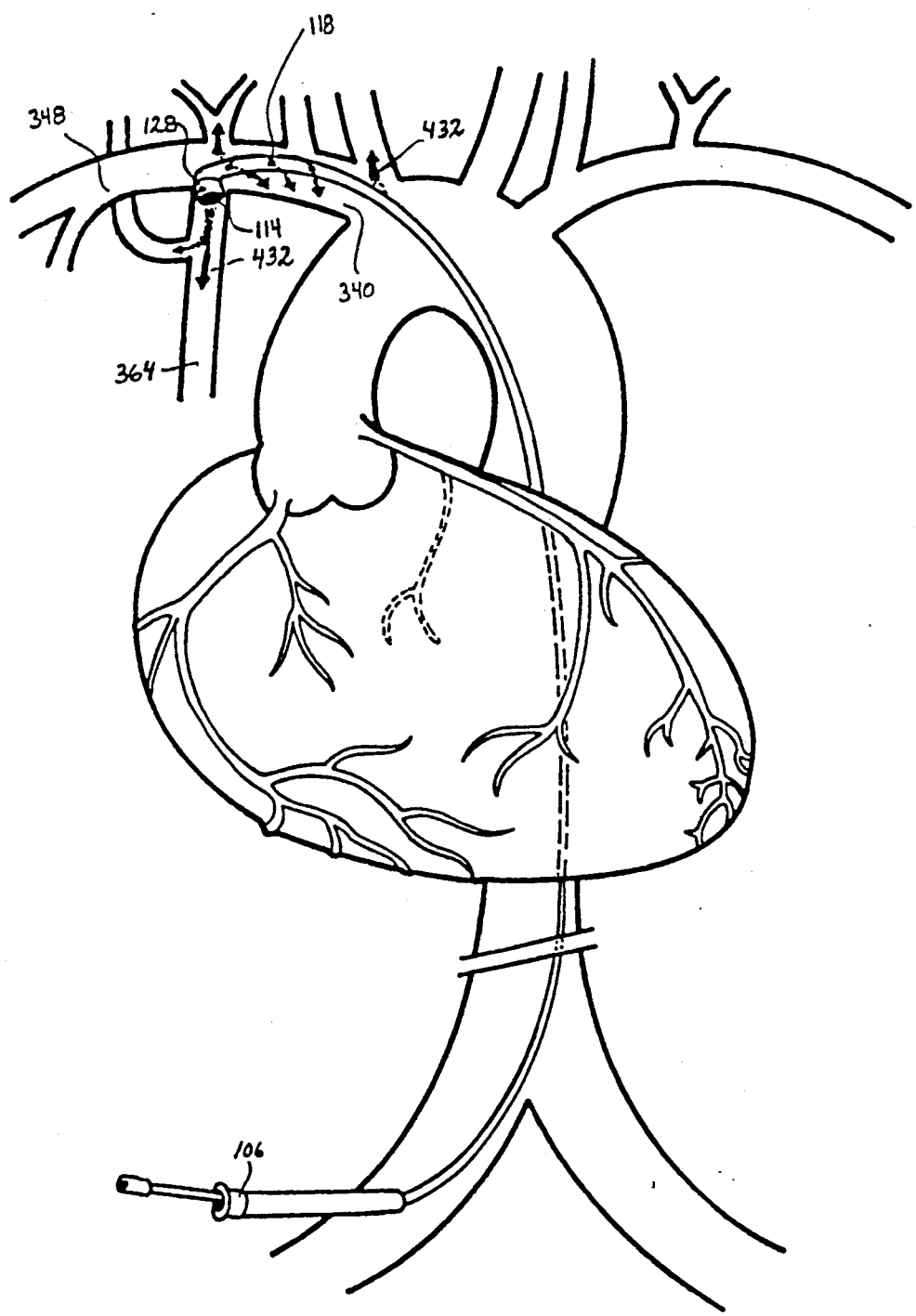
Figure 29:
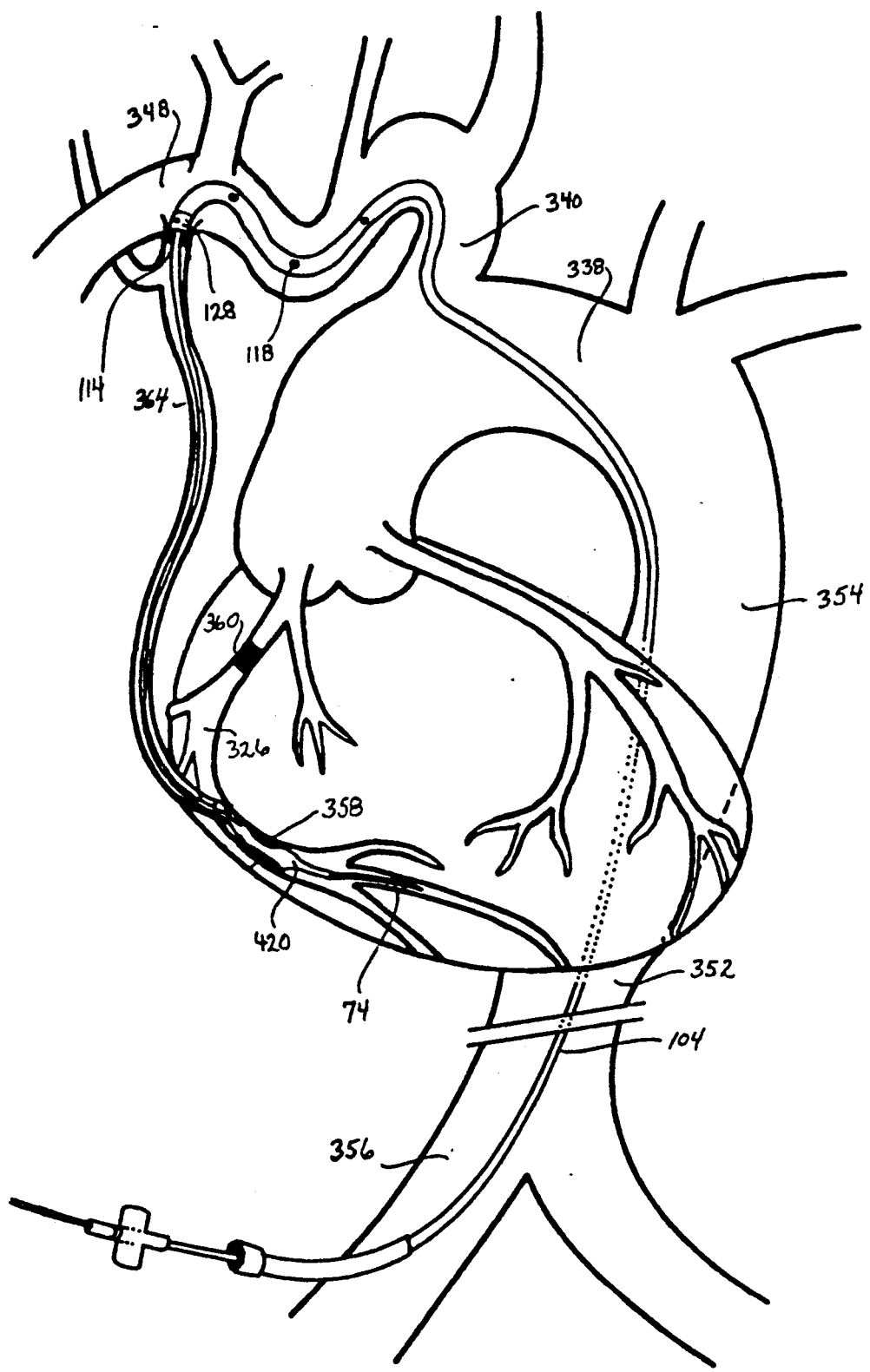
Figure 30:
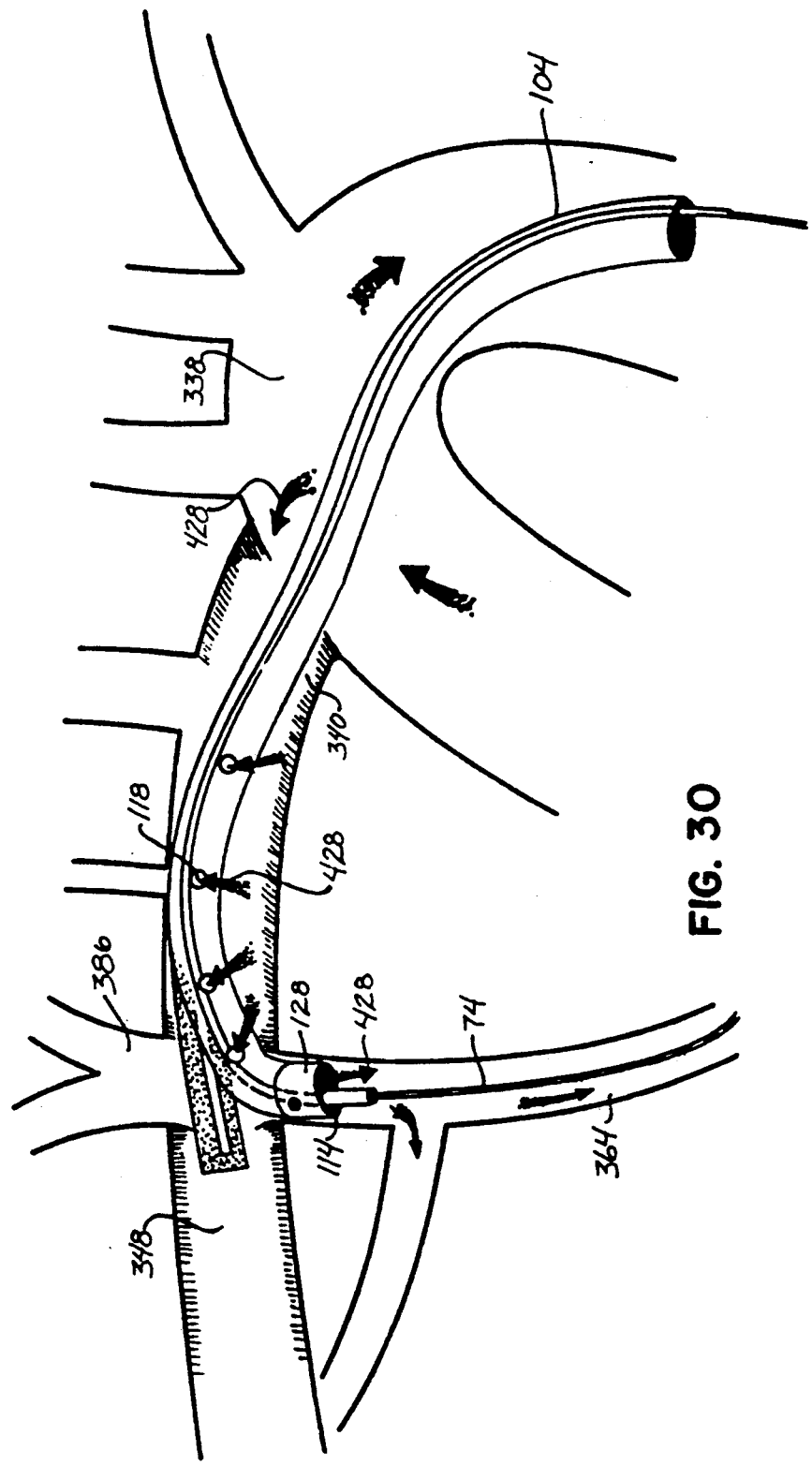
Figure 31:
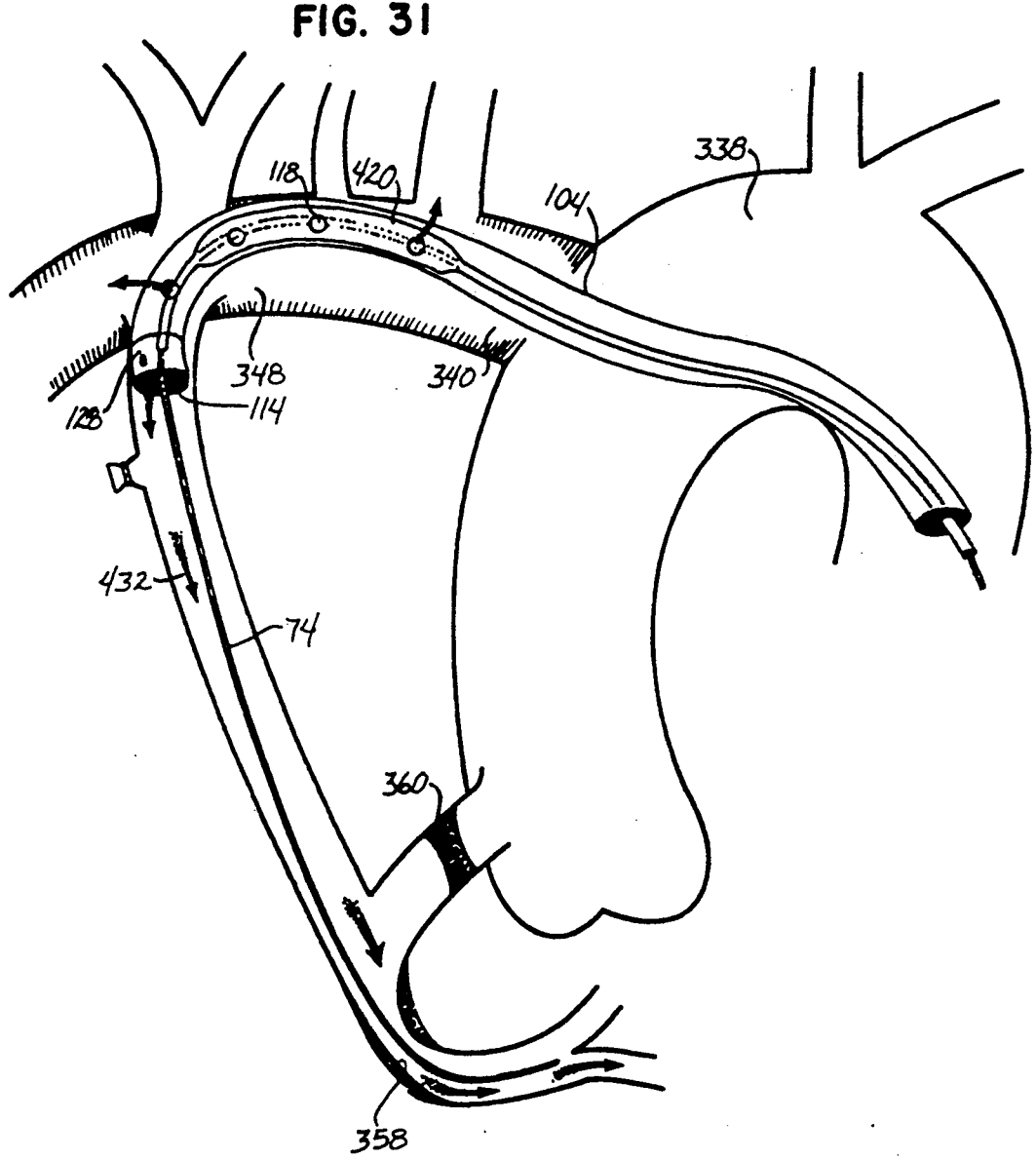
Figure 32:
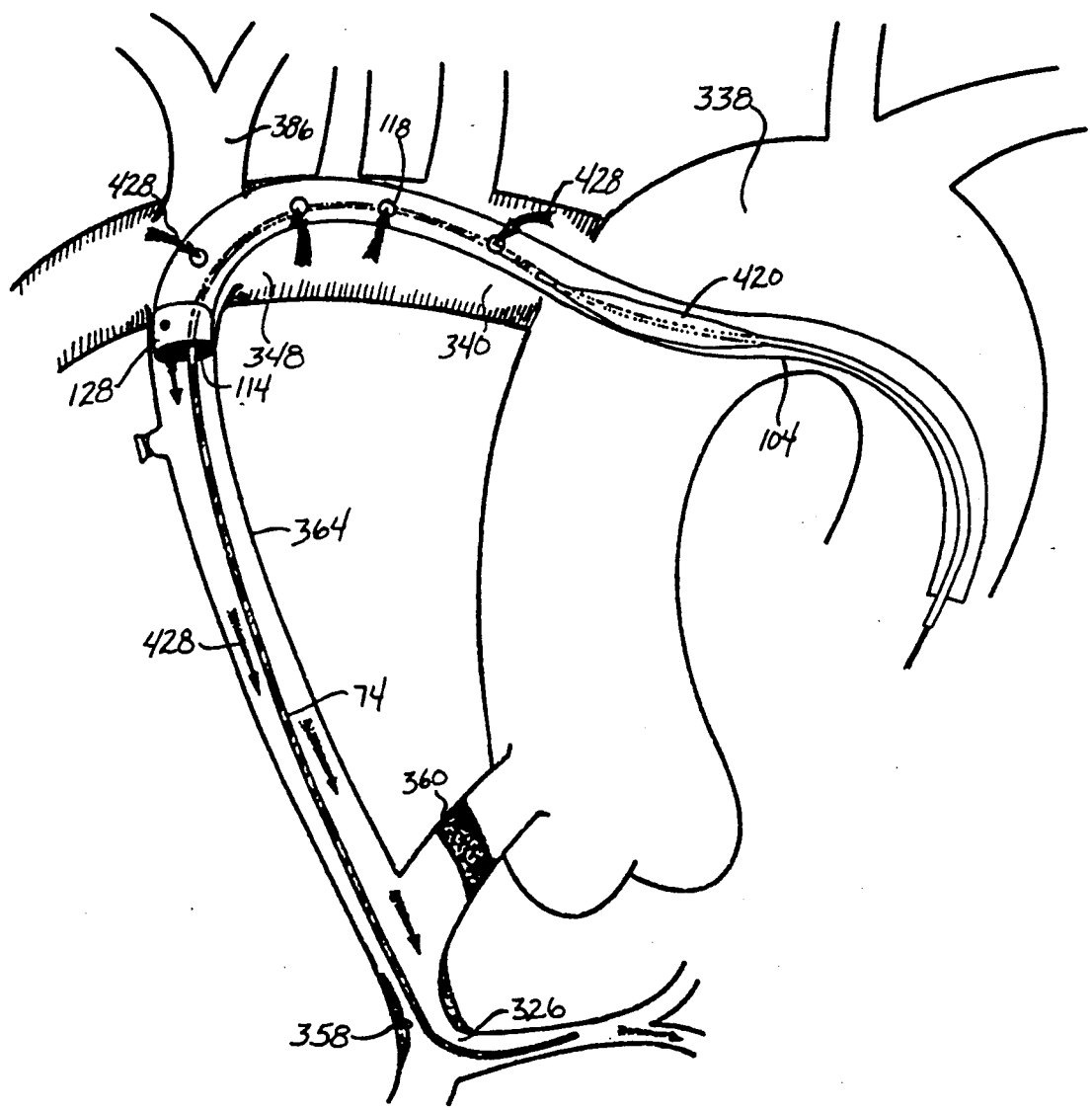

It has been discovered that after reduction of the vascular stenosis, shown in FIG. 16 at 168, the deflated balloon 172 has a somewhat larger residual diameter in that it does not completely deflate and wrap as it did before it was inflated the first time. This deflated balloon can be withdrawn into the invented guiding catheter 104 adjacent to side ports 118 while the guidewire 74 remains in the distal LAD 34 beyond the partially removed stenosis 168. This technical maneuver partially permits deflated balloon 172 to cover most of the sideholes and markedly reduces contrast exit through the side holes 118 and favors the dye exiting distal end port 114 into LITA 64 to maximize visualization in the area of the resolved LAD stenosis. Further withdrawal of the balloon into the catheter shaft, as shown in FIG. 17, will restore blood supply to LITA 64 via the uncovered side holes 118 and permit observation of the treated stenosis. This ensures that rapid closure does not occur, yet it provides fresh, oxygenated blood to the myocardium while the PTCA wire remains across the area of treatment.

The invention accordingly consists in the features of the construction, combinations of elements, and construction of parts which will be exemplified in the construction described above and of which the scope of the invention would be indicated in the following claims. It is to be understood that while certain embodiments of the present invention have been illustrated and described, the invention is not to be limited to these specific forms or arrangements of parts herein described and shown.

What is claimed is:

1. A catheter for selectively entering and visualizing normal and geriatrically displaced branch vessels of the arch of the aorta and internal thoracic artery origins comprising:

a catheter shaft having outer walls defining a central lumen, said outer walls comprising a first portion having a substantially linear shape in an X axis, a second portion extending at an angle toward a Y axis in a curved manner from said first portion and suitable for providing ease of passage for the catheter from a patient's aortic arch into one of the aortic arch branch vessels and a sub-branch of that vessel, and a third portion extending only toward a Z-axis at an out of plane angle relative to said first and second portions, into portion Z-axis orientation permitting hooked engagement of an internal thoracic artery origin.

2. A catheter according to claim 1 wherein the radius of the curve between said outer wall first portion and said outer wall second portion is between 5 mm and 25 mm.

3. A catheter according to claim 1 wherein the normally curved catheter shaft portions may be substantially straightened by passage of a wire through said central lumen.

4. A catheter according to claim 1 wherein said catheter third portion further comprises a deformable soft tip having a distal central aperture in flow through communication with said central lumen.

5. A catheter according to claim 1 wherein said outer walls define a plurality of apertures extending through said outer walls into said central lumen.

* * * * *